United States Patent [19]
Croteau et al.

[11] Patent Number: 6,083,731
[45] Date of Patent: Jul. 4, 2000

[54] RECOMBINANT MATERIALS AND METHODS FOR THE PRODUCTION OF LIMONENE HYDROXYLASES

[75] Inventors: Rodney Bruce Croteau, Pullman; Shari Lee Lupien, Colfax, both of Wash.; Frank Karp, Moscow, Id.

[73] Assignee: Washington State University Research Foundation, Pullman, Wash.

[21] Appl. No.: 08/881,784

[22] Filed: Jun. 24, 1997

[51] Int. Cl.$^7$ .............................. C12N 9/02; C12N 15/53
[52] U.S. Cl. .................. 435/189; 435/252.3; 435/320.1; 536/23.2
[58] Field of Search ................................. 435/189, 252.3, 435/320.1; 536/23.2

[56] References Cited

PUBLICATIONS

Alberts et al., *Molecular Biology of the Cell*, Second Ed., Garland Publishing, Inc., New York, NY, pp. 185–187 and 265–266 (1989).

Alonso et al., "Production and Characterization of Polyclonal Antibodies in Rabbits to 4S(Limonene Synthase from Spearmint (*Mentha spicata*)," *Arch. Biochem. Biophys.* 301(1):58–63 (1993).

Alonso et al., "Purification of 4S–Limonene Synthase, a Monoterpene Cyclase from the Glandular Trichomes of Peppermint (*Mentha x piperita*) and Spearmint (*Mentha spicata*)" *J. Biol. Chem.* 267(11):7582–7587 (1992).

Alonso and Croteau, "Comparison of Two Monoterpene Cyclases Isolated From Higher Plants; λ–Terpinene Synthase From *Thymus Vulgaris*, and Limonene Synthase From *Mentha x Piperita*," *Secondary–Metabolite Biosynthesis and Metabolism* (Petrosky and McCormick, eds.), Plenum Press, New York, NY, pp. 239–251 (1992).

Alonso and Croteau, "9. Prenyltransferases and Cyclases," *Methods Plant Biochem.* 9:239–260 (1993).

Ashby et al., in "Prenyltransferases: From Yeast to Man," *Molecular Biology of Atherosclerosis* (Attie, A.D., ed.), Elsevier Science Publishing Co., Inc., Amsterdam, pp. 27–34 (1990).

Bozak et al., "Sequence analysis of ripening–related cytochrome P–450 cDNAs from avocado fruit," *Proc. Natl. Acad. Sci. USA* 87:3904–3908 (1990).

Colby et al., 4S–Limonene Synthase from the Oil Glands of Spearmint (*Mentha spicata*), *J. Biol. Chem.* 268:23016–23024 (1993).

Colby et al., "Isolation and Characterization of cDNA Encoding Limonene Cyclase in Spearmint," *J. Cell Biochem.*, Suppl. 0, 16(F):230 (1992), Abstract Only.

Croteau and Cane, "[44] Monoterpene and Sesquiterpene Cyclases," *Methods of Enzymology* 110:383–405 (1985).

Croteau, "Biosynthesis and Catabolism of Monterpenoids," *Chem. Rev.* 87:929–954 (1987).

Croteau and Satterwhite, "Biosynthesis of Monoterpenes," *J. Biol. Chem.* 264(26):15309–15315 (1989).

Croteau, "Metabolism of Plant Monterpenes," *ISI Atlas of Science: Biochemistry*, 1:182–188 (1988).

Croteau and Johnson, "7. Biosynthesis of Terpenoids in Glandular Trichomes," *Biology and Chemistry of Plant Trichomes*, Rodriguez et al., Eds., Plenum Publishing Corporation (1984), pp. 133–185.h.

Croteau and Gershenzon, "Chapter Eight. Genetic Control of Monoterpene Biosynthesis in Mints (*Mentha: Lamiaceae*)" *Genetic Engineering of Plant Secondary Metabolism*, B.E. Ellis et al., Eds., Plenum Press, New York (1994), pp. 193–229.

Croteau, "the Biosynthesis of Limonene in Mentha Species," *In Progress in Flavour Precursor Studies* (P. Schreier and P. Winterhalter, Eds.), Proceedings of the International of the International Conference, Allured Publishing Corporation, Carol Stream, Illinois, pp. 113–122 (1993).

Croteau, "Terpene Metabolism in Mint," Mint Industry Research Coucil, Washington Mint Commission, *Technical Report Summary Statement*, Jan. 22–24, 1997 (13 pages).

Croteau, "Metabolism of Monoterpenes in Mint (Mentha) Species," *Planta Med.* 57(S1);10–14 (1991).

Facchini and Chappell, "Gene family for an elicitor–induced sesquiterpene cyclase in tobacco," *Proc. Natl. Acad. Sci. USA* 89:11088–11092 (1992).

(List continued on next page.)

*Primary Examiner*—Charles L. Patterson, Jr.
*Attorney, Agent, or Firm*—Christensen O'Connor Johnson & Kindness PLLC

[57] ABSTRACT cDNA encoding (–)-limonene-6-hydroxylase from spearmint and (–)-limonene-3-hydroxylase from peppermint have been isolated and sequenced, and the corresponding amino acid sequences have been determined. Accordingly, isolated DNA sequences are provided which code for the expression of (–)-limonene-6-hydroxylase from spearmint (SEQ ID No:1, from *Mentha spicata*) and (–)-limonene-3-hydroxylase from peppermint (SEQ ID No:8, from *Mentha piperita*). In other aspects, replicable recombinant cloning vehicles are provided which code for limonene hydroxylase or for a base sequence sufficiently complementary to at least a portion of the limonene hydroxylase DNA or RNA to enable hybridization therewith (e.g., antisense limonene hydroxylase RNA or fragments of complementary limonene hydroxylase DNA which are useful as polymerase chain reaction primers or as probes for limonene hydroxylase or related genes). In yet other aspects, modified host cells are provided that have been transformed, transfected, infected and/or injected with a recombinant cloning vehicle and/or DNA sequence encoding limonene hydroxylase. Thus, systems and methods are provided for the recombinant expression of limonene hydroxylase that may be used to facilitate the production, isolation and purification of significant quantities of recombinant limonene hydroxylase (or of the primary enzyme products, trans-carveol or trans-isopiperitenol, respectively) for subsequent use, to obtain expression or enhanced expression of limonene hydroxylase in plants to attain enhanced production of trans-carveol or trans-isopiperitenol as a predator or pathogen defense mechanism, or may be otherwise employed for the regulation or expression of limonene hydroxylase or the production of trans-carveol or trans-isopiperitenol.

14 Claims, 11 Drawing Sheets

PUBLICATIONS

Gershenzon et al., "Isolation of Secretory Cells from Plant Glandular Trichomes and Their Use in Biosynthetic Studies of Monoterpenes and Other Gland Products," *Anal. Biochem.* 200:130–138 (1992).

Gershenzon et al., "Chapter Ten. Biosynthetic Methods for Plant Natural Products: New Procedures for the Study of Glandular Trichome Constituents," *Modern Phytochemical Methods*, N.H. Fischer et al., Eds., Plenum Press, New York (1991), pp. 347–370.

Gershenzon and Croteau, "Chapter 5. Terpenoids," *Herbivores: Their Interactions with Secondary Plant Metabolites*, vol. I, 2nd Ed. (Rosenthal and Berenbaum, eds.), Academic Press, San Diego, CA, pp. 165–219 (1991).

Gershenzon and Croteau, in "Chapter Three. Regulation of Monoterpene Biosynthesis in Higher Plants," *Biochemistry of the Mevalonic Acid Pathway to Terpenoids* (Towers, G.H.N. and Stafford, H.A., eds.), Plenum Press, New York, NY, Ch. 3, pp. 99–160 (1990).

Harborne, "16 Recent advances in the ecological chemistry of plant terpenoids," *Ecological Chemistry and Biochemistry of Plant Terpenoids* (Harborne and Tomas–Barberan, eds.), Clarendon Press, Oxford, MA, pp. 399–426 (1991).

Hallahan and Croteau, "Monoterpene Biosynthesis: Mechanism and Stereochemistry of the Enzymatic Cyclization of Geranyl Pyrophosphate to Cis–(+)–and (+)–trans–Sabinene Hydrate," *Arch. Biochem. Biophys.* 269(1):313–326 (1989).

Karp and Croteau, "Role of Hydroxylases in Monoterpene Biosynthesis," *Bioflavour '87*, Walter de Gruyter & Co., Berlin (1988), pp. 173–198.

Karp et al., "Monoterpene Biosynthesis: Specificity of the Hydroxylations of (–)–Limonene by Enzyme Preparations from Peppermint (*Mentha piperita*), Spearmint (*Mentha spicata*), and Perilla (*Perilla frutescens*) Leaves," *Arch. Biochem. Biophys.* 276:219–226 (1990).

Karp and Croteau, "Hydroxylation of (–)–β–Pinene and (–)–α–Pinene by a Cytochrome P–450 System from Hyssop (*Hyssopus Officinalis*)," *Secondary–Metabolite Biosynthesis and Metabolism*, R.J. Petroski et al., Eds., Plenum Press, New York (1992), pp. 253–260.

Kjonaas and Croteau, "Demonstration that Limonene is the First Cyclic Intermediate in Biosynthesis of Oxygenated p–Menthane Monoterpenes in *Mentha piperita* and Other Mentha Species," *Arch. Biochem. Biophys.* 220(1):79–89 (1983).

Lanznaster and Croteau, "Dye–Ligand and Immobilized Metal Ion Interaction Chromatography for the Purification of Enzymes of Prenyl Pyrophosphate Metabolism," *Protein Express. Purif.* 2:69–74 (1991).

Lupien et al., "Cytochrome P450 Limonene Hydroxylases of Mentha Species," *Drug Metabolism and Drug Interactions*, N. Kingsley, Ed., Freund Publishing House, London, England (1995), pp. 245–260.

Math et al., "The crtE gene in *Erwinia herbicola* encodes geranylgeranyl diphosphate synthase," *Proc. Natl. Acad. Sci. USA* 89:6761–6764 (1992).

McGarvey and Croteau, "Overexpression and mutagenesis of 4S–limonene synthase from spearmint (*Mentha spicata*)," *Plant Physiology* 105(1):89 (1994), Abstract Only.

Mihaliak et al., "10. Cytochrome P–450 Terpene Hydroxylases," *Meth. Plant Biochem.* 9:261–279 (1993).

Ponnamperuma and Croteau, "Purification and Characterization of an NADPH–Cytochrome P450 (Cytochrome c) Reductase from Spearmint (*Mentha spicata*) Glandular Trichomes," *Arch. Biochem. Biophys.* 329(1):9–16 (1996).

Rajaonarivony et al., "Evidence for an Essential Histidine Residue in 4S–Limonene Synthase and Other Terpene Cyclases," *Arch. Biochem. Biophys.* 299(1):77–82 (1992).

Rajaonarivony et al., "Characterization and Mechanism of (4S)–Limonene Synthase, a Monoterpene Cyclase from the Glandular Trichomes of Peppermint (*Mentha x piperita*)," *Arch. Biochem. Biophys.* 296(1):49–57 (1992).

Satterwhite and Croteau, "Resolution of Monoterpene Enantiomers by Gas Chromatography," *J. Chromatogr.* 407:243–252 (1987).

Satterwhite and Croteau, "Applications of Gas Chromatography to the Study of Terpenoid Metabolism," *J. Chromatography* 452:61–73, Elsevier Science Publishers B.V., Amsterdam (1988).

Savage et al., "Monoterpene Synthases of *Pinus contorta* and Related Conifers," *J. Biol. Chem.* 269(6):4012–4020 (1994).

Kang et al., "Isolation of a Genomic Clone for Cytochrome P450 Oxidase from *Mentha piperita*," *Mol. Cells.* 3(3):283–288 (1993).

Lupien, S. et al. "Cytochrome P450 limonene hydroxylases of Mentha species" Drug Metabolism and Drug Interaction, Vol. 12, No. 3–4, pp. 245–260, 1995.

|  | | C-3 hydroxylase | C-6 hydroxylase |
|---|---|---|---|
| (+)-Limonene | Products: | (+)-*trans*-isopiperitenol (50%) | (+)-*cis*-carveol (25%) |
| (-)-*p*-Menth-1-ene | Products: | (-)-*trans*-isopiperitol (37%) | (-)-*trans*-carvotanacetol (74%) |
| (+)-*p*-Menth-1-ene | Products: | (+)-*trans*-piperitol (37%) | (+)-*cis*-carvotanacetol (30%)<br>(+)-*trans*-piperitol (31%) |

Fig. 2

```
                    Membrane Insertion Sequence
  1  KNKKETMELD LLSAIIILVA TYIVSLLINQ WRKSKSQQNL PPSPPKLPVI
              (V-8.2)                            Halt-transfer Signal

51  GHLHFLWGGL PQHVFRSIAQ KYGPVAHVQL GEVYSVVLSS AEAAKQAMKV

101  LDPNFADRFD GIGSRTMWYD KDDIIFSPYN DHWRQMRRIC VTELLSPKNV

151  RSFGYIRQEE IERLIRLLGS SGGAPVDVTE EVSKMSCVVV CRAAFGSVLK
                                              (V-8.1)

201  DQGSLAELVK ESLALASGFE LADLYPSSWL LNLLSLNKYR LQRMRRRLDH

251  ILDGFLEEHR EKKSGEFGGE DIVDVLFRMQ KGSDIKIPIT SNCIKGFIFD

301  TFSAGAETSS TTISWALSEL MRNPAKMAKV QAEVREALKG KTVVDLSEVQ

351  ELKYLRSVLK ETLRLHPPFP LIPRQSREEC EVNGYTIPAK TRIFINVWAI
                                              (V-8.3)

401  GRDPQYWEDP DTFRPERFDE VSRDFMGNDF EFIPFGAGRR ICPGLHFGLA
                                          Heme Binding Region

451  NVEIPLAQLL YHFDWKLPQG MTDADLDMTE TPGLSGPKKK NVCLVPTLYK

501  SP*PLRS*HN KTSKIVIII* LLLHFFYHVI LRSVL*RWPR FRFQFGSGTE

551  PSVTVLSKKR TVPPPLLCLR YKTHKIK*KK RYFFLKK
```

Fig. 3

```
   1  AAAAAACAAA AAAGAAACAA TGGAGCTCGA CCTTTTGTCG GCAATTATAA
                                                (LH-2)→
  51  TCCTTGTGGC AACCTACATC GTATCCCTCC TAATCAACCA ATGGCGAAAA
 101  TCGAAATCCC AACAAAACCT ACCTCCGAGC CCTCCGAAGC TGCCGGTGAT
 151  CGGCCACCTC CACTTCCTGT GGGGAGGGCT TCCCCAGCAC GTGTTTAGGA
 201  GCATAGCCCA GAAGTACGGG CCGGTGGCGC ACGTGCAGCT GGGAGAAGTG
 251  TACTCGGTGG TGCTGTCGTC GGCGGAGGCA GCGAAGCAGG CGATGAAGGT
 301  GCTGGACCCG AACTTCGCCG ACCGGTTCGA CGGCATCGGG TCCAGGACCA
 351  TGTGGTACGA CAAAGATGAC ATCATCTTCA GCCCTTACAA CGATCACTGG
 401  CGCCAGATGC GGAGGATCTG CGTGACAGAG CTGCTGAGCC CGAAGAACGT
 451  CAGGTCCTTC GGGTACATAA GGCAGGAGGA GATCGAGCGC CTCATCCGGC
 501  TGCTCGGGTC GTCGGGGGGA GCGCCGGTCG ACGTGACGGA GGAGGTGTCG
 551  AAGATGTCGT GTGTCGTCGT GTGCAGGGCG GCGTTCGGGA GTGTGCTCAA
            (LH-1)→
 601  GGACCAGGGT TCGTTGGCGG AGTTGGTGAA GGAGTCGCTG GCATTGGCGT
 651  CCGGGTTTGA GCTGGCGGAT CTCTACCCTT CCTCATGGCT CCTCAACCTG
 701  CTTAGCTTGA CAAGTACAG GTTGCAGAGG ATGCGCCGCC GCCTCGATCA
 751  CATCCTTGAT GGGTTCCTGG AGGAGCATAG GGAGAAGAAG AGCGGCGAGT
 801  TGTGAGGCGA GGACATCGTC GACGTTCTTT TCAGGATGCA GAAGGGCAGC
 851  GACATCAAAA TTCCCATTAC TTCCAATTGC ATCAAGGGTT TCATTTTCGA
 901  CACCTTCTCC GCGGGAGCTG AAACGTCTTC GACGACCATC TCATGGGCGT
 951  TGTCGGAACT GATGAGGAAT CCGGCGAAGA TGGCCAAGGT GCAGGCGGAG
1001  GTAAGAGAGG CGCTCAAGGG AAAGACAGTC GTGGATTTGA GCGAGGTGCA
1051  AGAGCTAAAA TACCTGAGAT CGGTGTTAAA GGAGACTCTG AGGCTGCACC
1101  CTCCCTTTCC ATTAATCCCA AGACAATCCA GGGAAGAATG CGAGGTTAAC
1151  GGGTACACGA TTCCGGCCAA AACTAGAATC TTCATCAACG TCTGGGCTAT
1201  CGGAAGGGAT CCCCAATACT GGGAAGATCC CGACACCTTC CGCCCTGAGA
```

Fig. 4A

```
1251  GATTCGATGA GGTTTCCAGG GATTTCATGG GAAACGATTT CGAGTTCATC
1301  CCATTCGGGG CGGGTCGAAG AATCTGCCCC GGTTTACATT TCGGGCTGGC
1351  AAATGTTGAG ATCCCATTGG CGCAACTGCT CTACCACTTC GACTGGAAAT
1401  TGCCACAAGG AATGACTGAT GCCGACTTGG ACATGACGGA GACCCCAGGT
1451  CTTTCTGGGC CAAAAAGAA AAATGTTTGC TTGGTTCCCA CACTCTATAA
1501  AAGTCCTTAA CCACTAAGAA GTTAGCATAA TAAGACATCT AAAATTGTCA
1551  TAÀTCATCTA ATTATTGTTA CACTTCTTCT ATCATGTCAT TTTGAGAAGT
1601  GTCTTATAGA GGTGGCCACG GTTCCGGTTC CAGTTCGGAA GCGGAACCGA
1651  ACCATCAGTT ACGGTCTCA GCAAGAAGCG AACCGTCCCG CCCCCCCTAC
1701  TGTGTTTGAG ATATAAACA CATAAAATAA AATAAAAAAA ACGCTATTTT
1751  TTTTTAAAAA AA
```

Fig. 4B

```
   1  AGAAAATAAA ATAAAATAAT GGAGCTTCAG ATTTCGTCGG CGATTATAAT
  51  CCTTGTAGTA ACCTACACCA TATCCCTCCT AATAATCAAG CAATGGCGAA
 101  AACCGAAACC CCAAGAGAAC CTGCCTCCGG GCCCGCCGAA GCTGCCGCTG
 151  ATCGGGCACC TCCACCTCCT ATGGGGAAG  CTGCCGCAGC ACGCGCTGGC
 201  CAGCGTGGCG AAGCAGTACG GCCCAGTGGC GCACGTGCAG CTCGGCGAGG
 251  TGTTCTCCGT CGTGCTCTCG TCCCGCGAGG CCACGAAGGA GGCGATGAAG
 301  CTGGTGGACC CGGCCTGCGC GGACCGGTTC GAGAGCATCG GGACGAAGAT
 351  CATGTGGTAC GACAACGACG ACATCATCTT CAGCCCCTAC AGCGTGCACT
 401  GGCGCCAGAT GCGGAAGATC TGCGTCTCCG AGCTCCTCAG CGCCCGCAAC
 451  GTCCGCTCCT TCGGCTTCAT CAGGCAGGAC GAGGTGTCCC GCCTCCTCGG
 501  CCACCTCCGC TCCTCGGCCG CGGCGGGGGA GGCCGTGGAC CTCACGGAGC
 551  GGATAGCGAC GCTGACGTGC TCCATCATCT GCAGGGCGGC GTTCGGGAGC
 601  GTGATCAGGG ACCACGAGGA GCTGGTGGAG CTGGTGAAGG ACGCCCTCAG
 651  CATGGCGTCC GGGTTCGAGC TCGCCGACAT GTTCCCCTCC TCCAAGCTCC
 701  TCAACTTGCT CTGCTGGAAC AAGAGCAAGC TGTGGAGGAT GCGCCGCCGC
 751  GTCGACGCCA TCCTCGAGGC CATCGTGGAG GAGCACAAGC TCAAGAAGAG
 801  CGGCGAGTTT GGCGGCGAGG ACATTATTGA CGTACTCTTT AGGATGCAGA
 851  AGGATAGCCA GATCAAAGTC CCCATCACCA CCAACGCCAT CAAAGCCTTC
 901  ATCTTCGACA CGTTCTCAGC GGGGACCGAG ACATCATCAA CCACCACCCT
 951  GTGGGTGATG GCGGAGCTGA TGAGGAATCC AGAGGTGATG GCGAAAGCGC
1001  AGGCGGAGGT GAGAGCGGCG CTGAAGGGGA AGACGGACTG GGACGTGGAC
1051  GACGTGCAGG AGCTTAAGTA CATGAAATCG GTGGTGAAGG AGACGATGAG
1101  GATGCACCCT CCGATCCCGT TGATCCCGAG ATCATGCAGA GAAGAATGCG
1151  AGGTCAACGG GTACACGATT CCGAATAAGG CCAGAATCAT GATCAACGTG
1201  TGGTCCATGG GTAGGAATCC TCTCTACTGG GAAAAACCCG AGACCTTTTG
1251  GCCCGAAAGG TTTGACCAAG TCTCGAGGGA TTTCATGGGA AACGATTTCG
1301  AGTTCATCCC ATTTGGAGCT GGAAGAAGAA TCTGCCCCGG TTTGAATTTC
1351  GGGTTGGCAA ATGTTGAGGT CCCATTGGCA CAGCTTCTTT ACCACTTCGA
1401  CTGGAAGTTG GCGGAAGGAA TGAAGCCTTC CGATATGGAC ATGTCTGAGG
1451  CAGAAGGCCT TACCGGAATA AGAAAGAACA ATCTTCTACT CGTTCCCACA
1501  CCCTACGATC CTTCCTCATG ATCAATTAAT ACTCTTTAAT TTGCTCCTTT
1551  GAATAAAGAG TGCATATACA TATATGATAT ATACACATAC ACACACATAT
1601  ACTATATATG TATATGTAGC TTTGGGCTAT GAATATAGAA ATTATGTAAA
1651  AAAAAAAAAA AAAAA
```

Fig. 5

```
Met Glu Leu Gln Ile Ser Ser Ala Ile Ile Ile Leu Val Val Thr Tyr
1               5                   10                  15

Thr Ile Ser Leu Leu Ile Ile Lys Gln Trp Arg Lys Pro Lys Pro Gln
            20              25              30

Glu Asn Leu Pro Pro Gly Pro Pro Lys Leu Pro Leu Ile Gly His Leu
            35              40              45

His Leu Leu Trp Gly Lys Leu Pro Gln His Ala Leu Ala Ser Val Ala
    50              55              60

Lys Gln Tyr Gly Pro Val Ala His Val Gln Leu Gly Glu Val Phe Ser
65              70              75              80

Val Val Leu Ser Ser Arg Glu Ala Thr Lys Phe Ala Met Lys Leu Val
            85              90              95

Asp Pro Ala Cys Ala Asp Arg Phe Glu Ser Ile Gly Thr Lys Ile Met
            100             105             110

Trp Tyr Asp Asn Asp Asp Ile Ile Phe Ser Pro Tyr Ser Val His Trp
        115             120             125

Arg Gln Met Arg Lys Ile Cys Val Ser Glu Leu Leu Ser Ala Arg Asn
    130             135             140

Val Arg Ser Phe Gly Phe Ile Arg Gln Asp Glu Val Ser Arg Leu Leu
145             150             155             160

Gly His Leu Arg Ser Ser Ala Ala Ala Gly Glu Ala Val Asp Leu Thr
            165             170             175

Glu Arg Ile Ala Thr Leu Thr Cys Ser Ile Ile Cys Arg Ala Ala Phe
            180             185             190

Gly Ser Val Ile Arg Asp His Glu Glu Leu Val Glu Leu Val Lys Asp
        195             200             205

Ala Leu Ser Met Ala Ser Gly Phe Glu Leu Ala Asp Met Phe Pro Ser
    210             215             220

Ser Lys Leu Leu Asn Leu Leu Cys Trp Asn Lys Ser Lys Leu Trp Arg
225             230             235             240

Met Arg Arg Arg Val Asp Ala Ile Leu Glu Ala Ile Val Glu Glu His
            245             250             255

Lys Leu Lys Lys Ser Gly Glu Phe Gly Gly Glu Asp Ile Ile Asp Val
            260             265             270

Leu Phe Arg Met Gln Lys Asp Ser Gln Ile Lys Val Pro Ile Thr Ile
        275             280             285
```

Fig. 6A

```
Asn Ala Ile Lys Ala Phe Ile Phe Asp Thr Phe Ser Ala Gly Thr Glu
    290             295             300
Thr Ser Ser Thr Thr Thr Leu Trp Val Met Ala Glu Leu Met Arg Asn
305             310             315                 320
Pro Glu Val Met Ala Lys Ala Gln Ala Glu Val Arg Ala Ala Leu Lys
            325             330                 335
Gly Lys Thr Asp Trp Asp Val Asp Val Gln Glu Leu Lys Tyr Met
            340             345             350
Lys Ser Val Val Lys Glu Ile Met Arg Met His Pro Pro Ile Pro Leu
        355             360             365
Ile Pro Arg Ser Cys Arg Glu Glu Cys Glu Val Asn Gly Tyr Thr Ile
    370             375             380
Pro Asn Lys Ala Arg Ile Met Ile Asn Val Trp Ser Met Gly Arg Asn
385             390             395                 400
Pro Leu Tyr Trp Glu Lys Pro Glu Thr Phe Trp Pro Glu Arg Phe Asp
            405             410             415
Gln Val Ser Arg Asp Phe Met Gly Asn Asp Phe Glu Phe Ile Pro Phe
            420         425             430
Gly Ala Gly Arg Arg Ile Cys Pro Gly Leu Asn Phe Gly Leu Ala Asn
        435             440             445
Val Glu Val Pro Leu Ala Gln Leu Leu Tyr His Phe Asp Trp Lys Leu
    450             455             460
Ala Glu Gly Met Asn Pro Ser Asp Met Asp Met Ser Glu Ala Glu Gly
465             470             475                 480
Leu Thr Gly Ile Arg Lys Asn Asn Leu Leu Leu Val Pro Thr Pro Tyr
            485             490             495
Asp Pro Ser Ser
            500
```

Fig. 6B

```
SM    1 KNKKETMELDLLSAIIILVATYIVSLL.INQWRKSKSQQNLPPSPPKLPV  49
        :  . ||| : ||||||| || :||| | |||| | |:|||| ||||.
PM    1 RK*NKIMELQISSAIIILVVTYTISLLIIKQWRKPKPQENLPPGPPKLPL  50

SM   50 IGHLHFLWGGLPQHVFRSIAQKYGPVAHVQLGEVYSVVLSSAEAAKQAMK  99
        ||||| ||| ||||    |:|..||||||||||||:|||||| || |:|||
PM   51 IGHLHLLWGKLPQHALASVAKQYGPVAHVQLGEVFSVVLSSREATKEAMK 100

SM  100 VLDPNFADRFDGIGSRTMWYDKDDIIFSPYNDHWRQMRRICVTELLSPKN 149
        ..||  ||||: ||.: |||| ||||||||. ||||||:|||.|||| :|
PM  101 LVDPACADRFESIGTKIMWYDNDDIIFSPYSVHWRQMRKICVSELLSARN 150

SM  150 VRSFGYIRQEEIERLIRLLGSS..GGAPVDVTEEVSKMSCVVVCRAAFGS 197
        |||||:|||:|: ||:  | ||   | ||.|| :. :.| ::||||||||
PM  151 VRSFGFIRQDEVSRLLGHLRSSAAAGEAVDLTERIATLTCSIICRAAFGS 200

SM  198 VLKDQGSLAELVKESLALASGFELADLYPSSWLLNLLSLNKYRLQRMRRR 247
        |::|   |  ||||:.|.:|||||||||::|||  ||||| || :| |||||
PM  201 VIRDHEELVELVKDALSMASGFELADMFPSSKLLNLLCWNKSKLWRMRRR 250

SM  248 LDHILDGFLEEHREKKSGEFGGEDIVDVLFRMQKGSDIKIPITSNCIKGF 297
        .|  ||:  .|||:  |||||||||||:|||||||||  |  ||:|||.|  ||  |
PM  251 VDAILEAIVEEHKLKKSGEFGGEDIIDVLFRMQKDSQIKVPITTNAIKAF 300

SM  298 IFDTFSAGAETSSTTISWALSELMRNPAKMAKVQAEVREALKGKTVVDLS 347
        |||||||| ||||||  | :.||||||  ||| ||||| |||||| |.
PM  301 IFDTFSAGTETSSTTTLWVMAELMRNPEVMAKAQAEVRAALKGKTDWDVD 350

SM  348 EVQELKYLRSVLKETLRLHPPFPLIPRQSREECEVNGYTIPAKTRIFINV 397
        :||||||::||.|||:|||  |||||  |||||||||||||||| | || |||
PM  351 DVQELKYMKSVVKETMRMHPPIPLIPRSCREECEVNGYTIPNKARIMINV 400

SM  398 WAIGRDPQYWEDPDTFRPERFDEVSRDFMGNDFEFIPFGAGRRICPGLHF 447
        |..||.| ||| |:|| |||||:||||||||||||||||||||||||||.|
PM  401 WSMGRNPLYWEKPETFWPERFDQVSRDFMGNDFEFIPFGAGRRICPGLNF 450

SM  448 GLANVEIPLAQLLYHFDWKLPQGMTDADLDMTETPGLSGPKKKNVCLVPT 497
        ||||||:||||||||||||||| :||  .|:||.|  ||.| :| |. ||||
PM  451 GLANVEVPLAQLLYHFDWKLAEGMKPSDMDMSEAEGLTGIRKNNLLLVPT 500

SM  498 LYKSP*P.....LRS*HNKTSKIVIII*LLLHFFYHVILRSVL*RWPRFR 542
        |            .  ||   :   |   |:|   |    ||       :
PM  501 PYDPSS*SINTL*FAPLNKECIYIYDIYTYTHIYYICICSFGL*I*KLCK 550

SM  543 FQFGSGTEPSVTVLSKKRTVPPPLLCLRYKTHKIK*KKRYFFLKK 587
PM  551 KKKKK........................................ 555
```

Fig. 7

```
                         SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
          (A) LENGTH: 496 amino acids
          (B) TYPE: amino acid
          (C) STRANDEDNESS:
          (D) TOPOLOGY: linear (ii) MOLECULE TYPE: protein (vi) ORIGINAL SOURCE:
          (A) ORGANISM: Mentha spicata (vii) IMMEDIATE SOURCE:
          (B) CLONE: SM12.2

(ix) FEATURE:
          (A) NAME/KEY: Cleavage-site
          (B) LOCATION: 7..27
          (D) OTHER INFORMATION: /note= "V-8.2 proteolytic fragment"

(ix) FEATURE:
          (A) NAME/KEY: Active-site
          (B) LOCATION: 7..48
          (D) OTHER INFORMATION: /note= "Membrane insertion
              sequence"

(ix) FEATURE:
          (A) NAME/KEY: Active-site
          (B) LOCATION: 44..48
          (D) OTHER INFORMATION: /note= "Halt-transfer signal"

(ix) FEATURE:
          (A) NAME/KEY: Cleavage-site
          (B) LOCATION: 182..206
          (D) OTHER INFORMATION: /note= "V-8.1 proteolytic fragment"

(ix) FEATURE:
          (A) NAME/KEY: Cleavage-site
          (B) LOCATION: 380..404
          (D) OTHER INFORMATION: /note= "V-8.3 proteolytic fragment"
```

(ix) FEATURE:
        (A) NAME/KEY: Binding-site
        (B) LOCATION: 429..454
        (D) OTHER INFORMATION: /note= "Heme binding region"

(xi) SEQUENCE DESCRIPTION: SEQ ID NO:1:

Met Glu Leu Asp Leu Leu Ser Ala Ile Ile Ile Leu Val Ala Thr Tyr
1               5                   10                  15

Ile Val Ser Leu Leu Ile Asn Gln Trp Arg Lys Ser Lys Ser Gln Gln
                20                  25                  30

Asn Leu Pro Pro Ser Pro Pro Lys Leu Pro Val Ile Gly His Leu His
            35                  40                  45

Phe Leu Trp Gly Gly Leu Pro Gln His Val Phe Arg Ser Ile Ala Gln
    50                  55                  60

Lys Tyr Gly Pro Val Ala His Val Gln Leu Gly Glu Val Tyr Ser Val
65              70                  75                  80

Val Leu Ser Ser Ala Glu Ala Lys Gln Ala Met Lys Val Leu Asp
                85                  90                  95

Pro Asn Phe Ala Asp Arg Phe Asp Gly Ile Gly Ser Arg Thr Met Trp
            100                 105                 110

Tyr Asp Lys Asp Ile Ile Phe Ser Pro Tyr Asn Asp His Trp Arg
    115                 120                 125

Gln Met Arg Arg Ile Cys Val Thr Glu Leu Leu Ser Pro Lys Asn Val
    130                 135                 140

Arg Ser Phe Gly Tyr Ile Arg Gln Glu Glu Ile Glu Arg Leu Ile Arg
145                 150                 155                 160

Leu Leu Gly Ser Ser Gly Gly Ala Pro Val Asp Val Thr Glu Val
                165                 170                 175

Ser Lys Met Ser Cys Val Val Cys Arg Ala Ala Phe Gly Ser Val
                180                 185                 190

Leu Lys Asp Gln Gly Ser Leu Ala Glu Leu Val Lys Glu Ser Leu Ala
                195                 200                 205

Leu Ala Ser Gly Phe Glu Leu Ala Asp Leu Tyr Pro Ser Ser Trp Leu
    210                 215                 220

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
            245                 250                 255

Lys Ser Gly Glu Phe Gly Gly Asp Ile Val Asp Val Leu Phe Arg
                260                 265                 270

Met Gln Lys Gly Ser Asp Ile Lys Ile Pro Ile Thr Ser Asn Cys Ile
    275                 280                 285

Lys Gly Phe Ile Phe Asp Thr Phe Ser Ala Gly Ala Glu Thr Ser Ser
    290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
            340                 345                 350

Leu Lys Glu Thr Leu Arg Leu His Pro Pro Phe Pro Leu Ile Pro Arg
    355                 360                 365

Gln Ser Arg Glu Glu Cys Glu Val Asn Gly Tyr Thr Ile Pro Ala Lys
370                 375                 380

```
Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
            405                 410                 415

Arg Asp Phe Met Gly Asn Asp Phe Glu Phe Ile Pro Phe Gly Ala Gly
            420                 425                 430

Arg Arg Ile Cys Pro Gly Leu His Phe Gly Leu Ala Asn Val Glu Ile
            435                 440                 445

Pro Leu Ala Gln Leu Leu Tyr His Phe Asp Trp Lys Leu Pro Gln Gly
450                 455                 460

Met Thr Asp Ala Asp Leu Leu Met Thr Glu Thr Pro Gly Leu Ser Gly
465                 470                 475                 480

Pro Lys Lys Lys Asn Val Cys Leu Val Pro Thr Leu Tyr Lys Ser Pro
            485                 490                 495
```

(2) INFORMATION FOR SEQ ID NO:2:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..25
        (D) OTHER INFORMATION: /note= "proteolytic fragment V-8.1"

(xi) SEQUENCE DESCRIPTION: SEQ ID NO:2:

```
Val Ser Lys Met Ser Cys Val Val Val Cys Arg Ala Ala Phe Gly Ser
1               5                   10                  15

Val Leu Lys Asp Gln Gly Ser Leu Ala
                20                  25
```

(2) INFORMATION FOR SEQ ID NO:3:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..21
        (D) OTHER INFORMATION: /note= "proteolytic fragment V-8.2"

(xi) SEQUENCE DESCRIPTION: SEQ ID NO:3:

```
Met Glu Leu Asp Leu Leu Ser Ala Ile Ile Ile Leu Val Ala Thr Tyr
1               5                   10                  15

Ile Val Ser Leu Leu
                20
```

(2) INFORMATION FOR SEQ ID NO:4:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (ix) FEATURE:
    (A) NAME/KEY: Peptide
    (B) LOCATION: 1..24
    (D) OTHER INFORMATION: /note= "proteolytic fragment V-8.3"

(xi) SEQUENCE DESCRIPTION: SEQ ID NO:4:

Glu Val Asn Gly Tyr Thr Ile Pro Ala Lys Thr Arg Ile Phe Ile Asn
1               5                   10                  15

Val Trp Ala Ile Gly Arg Asp Pro
            20

(2) INFORMATION FOR SEQ ID NO:5:

(i) SEQUENCE CHARACTERISTICS:
        (A) LENGTH: 1762 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Mentha spicata
        (C) INDIVIDUAL ISOLATE: cDNA encoding
            (-)-limonene-6-hydroxylase (vii) IMMEDIATE SOURCE:
        (B) CLONE: pSM12.2

(ix) FEATURE:
        (A) NAME/KEY: misc_feature
        (B) LOCATION: 558..1212
        (D) OTHER INFORMATION: /product= "Probe LH-1 (Figure 4A)"

(ix) FEATURE:
        (A) NAME/KEY: misc_feature
        (B) LOCATION: 39..538
        (D) OTHER INFORMATION: /product= "Probe LH-2 (Figure 4A)"

(xi) SEQUENCE DESCRIPTION: SEQ ID NO:5:

```
AAAAAACTAA AAAGAAACAA TGGAGCTCGA CCTTTTGTCG GCAATTATAA TCCTTGTGGC      60

AACCTACATC GTATCCCTCC TAATCAACCA ATGGCGAAAA TCGAAATCCC AACAAAACCT     120

ACCTCCGAGC CCTCCGAAGC TGCCGGTGAT CGGCCACCTC CACTTCCTGT GGGGAGGGCT     180

TCCCCAGCAC GTGTTTAGGA GCATAGCCCA GAAGTACGGG CCGGTGGCGC ACGTGCAGCT     240

GGGAGAAGTG TACTCGGTGG TGCTGTCGTC GGCGGAGGCA GCGAAGCAGG CGATGAAGGT     300

GCTGGACCCG AACTTCGCCG ACCGGTTCGA CGGCATCGGG TCCAGGACCA TGTGGTACGA     360

CAAAGATGAC ATCATCTTCA GCCCTTACAA CGATCACTGG CGCCAGATGC GGAGGATCTG     420

CGTGACAGAG CTGCTGAGCC CGAAGAACGT CAGGTCCTTC GGGTACATAA GGCAGGAGGA     480

GATCGAGCGC CTCATCCGGC TGCTCGGGTC GTCGGGGGGA GCGCCGGTCG ACGTGACGGA     540

GGAGGTGTCG AAGATGTCGT GTGTCGTCGT GTGCAGGGCG GCGTTCGGGA GTGTGCTCAA     600

GGACCAGGGT TCGTTGGCGG AGTTGGTGAA GGAGTCGCTG GCATTGGCGT CCGGGTTTGA     660

GCTGGCGGAT CTCTACCCTT CCTCATGGCT CCTCAACCTG CTTAGCTTGA ACAAGTACAG     720

GTTGCAGAGG ATGCGCCGCC GCCTCGATCA CATCCTTGAT GGGTTCCTGG AGGAGCATAG     780

GGAGAAGAAG AGCGGCGAGT TTGGAGGCGA GGACATCGTC GACGTTCTTT TCAGGATGCA     840

GAAGGGCAGC GACATCAAAA TTCCCATTAC TTCCAATTGC ATCAAGGGTT TCATTTTCGA     900

CACCTTCTCC GCGGGAGCTG AAACGTCTTC GACGACCATC TCATGGGCGT TGTCGGAACT     960

GATGAGGAAT CCGGCGAAGA TGGCCAAGGT GCAGGCGGAG GTAAGAGAGG CGCTCAAGGG    1020
```

```
AAAGACAGTC GTGGATTTGA GCGAGGTGCA AGAGCTAAAA TACCTGAGAT CGGTGTTAAA      1080

GGAGACTCTG AGGCTGCACC CTCCCTTTCC ATTAATCCCA AGACAATCCA GGGAAGAATG      1140

CGAGGTTAAC GGGTACACGA TTCCGGCCAA AACTAGAATC TTCATCAACG TCTGGGCTAT      1200

CGGAAGGGAT CCCCAATACT GGGAAGATCC CGACACCTTC CGCCCTGAGA GATTCGATGA      1260

GGTTTCCAGG GATTTCATGG GAAACGATTT CGAGTTCATC CCATTCGGGG CGGGTCGAAG      1320

AATCTGCCCC GGTTTACATT TCGGGCTGGC AAATGTTGAG ATCCCATTGG CGCAACTGCT      1380

CTACCACTTC GACTGGAAAT TGCCACAAGG AATGACTGAT GCCGACTTGG ACATGACGGA      1440

GACCCCAGGT CTTTCTGGGC AAAAAAGAA AAATGTTTGC TTGGTTCCCA CACTCTATAA       1500

AAGTCCTTAA CCACTAAGAA GTTAGCATAA TAAGACATCT AAAATTGTCA TAATCATCTA      1560

ATTATTGTTA CACTTCTTCT ATCATGTCAT TTTGAGAAGT GTCTTATAGA GGTGGCCACG      1620

GTTCCGGTTC CAGTTCGGAA GCGGAACCGA ACCATCAGTT ACGGTTCTCA GCAAGAAGCG      1680

AACCGTCCCG CCCCCCCTAC TGTGTTTGAG ATATAAAACA CATAAAATAA AATAAAAAAA      1740

ACGCTATTTT TTTTTAAAAA AA                                              1762
```

(2) INFORMATION FOR SEQ ID NO:6:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Mentha spicata (vii) IMMEDIATE SOURCE:
        (B) CLONE: pSM12.2

(ix) FEATURE:
        (A) NAME/KEY: misc_feature
        (B) LOCATION: 1..655
        (D) OTHER INFORMATION: /product= "Probe LH-1 (Figure 4A)"

(xi) SEQUENCE DESCRIPTION: SEQ ID NO:6:

```
CGTGTGTCGT CGTGTGCAGG GCGGCGTTCG GGAGTGTGCT CAAGGACCAG GGTTCGTTGG       60

CGGAGTTGGT GAAGGAGTCG CTGGCATTGG CGTCCGGGTT TGAGCTGGCG GATCTCTACC      120

CTTCCTCATG GCTCCTCAAC CTGCTTAGCT TGAACAAGTA CAGGTTGCAG AGGATGCGCC      180

GCCGCCTCGA TCACATCCTT GATGGGTTCC TGGAGGAGCA TAGGGAGAAG AAGAGCGGCG      240

AGTTGTGAGG CGAGGACATC GTCGACGTTC TTTTCAGGAT GCAGAAGGGC AGCGACATCA      300

AAATTCCCAT TACTTCCAAT TGCATCAAGG GTTTCATTTT CGACACCTTC TCCGCGGGAG      360

CTGAAACGTC TTCGACGACC ATCTCATGGG CGTTGTCGGA ACTGATGAGG AATCCGGCGA      420

AGATGGCCAA GGTGCAGGCG GAGGTAAGAG AGGCGCTCAA GGGAAAGACA GTCGTGGATT      480

TGAGCGAGGT GCAAGAGCTA AAATACCTGA GATCGGTGTT AAAGGAGACT CTGAGGCTGC      540

ACCCTCCCTT TCCATTAATC CCAAGACAAT CCAGGGAAGA ATGCGAGGTT AACGGGTACA      600

CGATTCCGGC CAAAACTAGA ATCTTCATCA ACGTCTGGGC TATCGGAAGG GATCC          655
```

(2) INFORMATION FOR SEQ ID NO:7:

(i) SEQUENCE CHARACTERISTICS:
        (A) LENGTH: 480 base pairs
        (B) TYPE: nucleic acid
        (C) STRANDEDNESS: single (D) TOPOLOGY: linear (ii) MOLECULE TYPE: cDNA fragment (vi) ORIGINAL SOURCE:
            (A) ORGANISM: Mentha spicata
            (C) INDIVIDUAL ISOLATE: cDNA encoding
                (-)-limonene-6-hydroxylase (vii) IMMEDIATE SOURCE:
            (B) CLONE: pSM12.2

(ix) FEATURE:
            (D) OTHER INFORMATION: cDNA probe LH-2

(xi) SEQUENCE DESCRIPTION: SEQ ID NO:7:

```
CGGCAATTAT AATCCTTGTG CAACCTACA TCGTATCCCT CCTAATCAAC CAATGGCGAA      60

AATCGAAATC CCAACAAAAC CTACCTCCGA GCCCTCCGAA GCTGCCGGTG ATCGGCCACC     120

TCCACTTCCT GTGGGGAGGG CTTCCCCAGC ACGTGTTTAG GAGCATAGCC CAGAAGTACG     180

GGCCGGTGGC GCACGTGCAG CTTACTCGGT GGTGCTGTCG TCGGCGGAGG CAGCGAAGCA     240

GGCGATGAAG GTGCTGGACC CGAACTTCGC CGACCGGTTC GACGGCATCG GGTCCAGGAC     300

CATGTGGTAC GACAAAGATG ACATCATCTT CAGCCCTTAC AACGATCACT GGCGCCAGAT     360

GCGGAGGATC TGCGTGACAG AGCTGCTGAG CCCGAAGAAC GTCAGGTCCT TCGGGTACAT     420

AAGGCAGGAG GAGATCGAGC GCTGCTCGGG TCGTCGGGGG GAGCGCCGGT CGACGTGACG     480
```

(2) INFORMATION FOR SEQ ID NO:8:

(i) SEQUENCE CHARACTERISTICS:
            (A) LENGTH: 1665 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Mentha x piperita (vii) IMMEDIATE SOURCE:
            (B) CLONE: pPM17

(xi) SEQUENCE DESCRIPTION: SEQ ID NO:8:

```
AGAAAATAAA ATAAAATAAT GGAGCTTCAG ATTTCGTCGG CGATTATAAT CCTTGTAGTA      60

ACCTACACCA TATCCCTCCT AATAATCAAG CAATGGCGAA AACCGAAACC CCAAGAGAAC     120

CTGCCTCCGG GCCCGCCGAA GCTGCCGCTG ATCGGGCACC TCCACCTCCT ATGGGGGAAG     180

CTGCCGCAGC ACGCGCTGGC CAGCGTGGCG AAGCAGTACG GCCCAGTGGC GCACGTGCAG     240

CTCGGCGAGG TGTTCTCCGT CGTGCTCTCG TCCCGCGAGG CCACGAAGGA GGCGATGAAG     300

CTGGTGGACC CGGCCTGCGC GGACCGGTTC GAGAGCATCG GACGAAGAT CATGTGGTAC     360

GACAACGACG ACATCATCTT CAGCCCCTAC AGCGTGCACT GGCGCCAGAT GCGGAAGATC     420

TGCGTCTCCG AGCTCCTCAG CGCCCGCAAC GTCCGCTCCT TCGGCTTCAT CAGGCAGGAC     480

GAGGTGTCCC GCCTCCTCGG CCACCTCCGC TCCTCGGCCG CGGCGGGGA GGCCGTGGAC     540

CTCACGGAGC GGATAGCGAC GCTGACGTGC TCCATCATCT GCAGGCGGC GTTCGGGAGC     600

GTGATCAGGG ACCACGAGGA GCTGGTGGAG CTGGTGAAGG ACGCCCTCAG CATGGCGTCC     660

GGGTTCGAGC TCGCCGACAT GTTCCCCTCC TCCAAGCTCC TCAACTTGCT CTGCTGGAAC     720

AAGAGCAAGC TGTGGAGGAT GCGCCGCCGC GTCGACGCCA TCCTCGAGGC CATCGTGGAG     780

GAGCACAAGC TCAAGAAGAG CGGCGAGTTT GGCGGCGAGG ACATTATTGA CGTACTCTTT     840
```

```
AGGATGCAGA AGGATAGCCA GATCAAAGTC CCCATCACCA CCAACGCCAT CAAAGCCTTC    900

ATCTTCGACA CGTTCTCAGC GGGGACCGAG ACATCATCAA CCACCACCCT GTGGGTGATG    960

GCGGAGCTGA TGAGGAATCC AGAGGTGATG GCGAAAGCGC AGGCGGAGGT GAGAGCGGCG   1020

CTGAAGGGGA AGACGGACTG GGACGTGGAC GACGTGCAGG AGCTTAAGTA CATGAAATCG   1080

GTGGTGAAGG AGACGATGAG GATGCACCCT CCGATCCCGT TGATCCCGAG ATCATGCAGA   1140

GAAGAATGCG AGGTCAACGG GTACACGATT CCGAATAAGG CCAGAATCAT GATCAACGTG   1200

TGGTCCATGG GTAGGAATCC TCTCTACTGG GAAAAACCCG AGACCTTTTG GCCCGAAAGG   1260

TTTGACCAAG TCTCGAGGGA TTTCATGGGA AACGATTTCG AGTTCATCCC ATTTGGAGCT   1320

GGAAGAAGAA TCTGCCCCGG TTTGAATTTC GGGTTGGCAA ATGTTGAGGT CCCATTGGCA   1380

CAGCTTCTTT ACCACTTCGA CTGGAAGTTG GCGGAAGGAA TGAACCCTTC CGATATGGAC   1440

ATGTCTGAGG CAGAAGGCCT TACCGGAATA AGAAAGAACA ATCTTCTACT CGTTCCCACA   1500

CCCTACGATC CTTCCTCATG ATCAATTAAT ACTCTTTAAT TTGCTCCTTT GAATAAAGAG   1560

TGCATATACA TATATGATAT ATACACATAC ACACACATAT ACTATATATG TATATGTAGC   1620

TTTGGGCTAT GAATATAGAA ATTATGTAAA AAAAATAAAA AGGAA                  1665

(2) INFORMATION FOR SEQ ID NO:9:

(i) SEQUENCE CHARACTERISTICS:
        (A) LENGTH: 500 amino acids
        (B) TYPE: amino acid
        (D) TOPOLOGY: linear (ii) MOLECULE TYPE: protein (vi) ORIGINAL SOURCE:
        (A) ORGANISM: Mentha x piperita
        (B) STRAIN: PM17
        (C) INDIVIDUAL ISOLATE: (-)-limonene-3-hydroxylase (xi) SEQUENCE DESCRIPTION: SEQ ID NO:9:

Met Glu Leu Gln Ile Ser Ser Ala Ile Ile Ile Leu Val Val Thr Tyr
1               5                   10                  15

Thr Ile Ser Leu Leu Ile Ile Lys Gln Trp Arg Lys Pro Lys Pro Gln
            20                  25                  30

Glu Asn Leu Pro Pro Gly Pro Pro Lys Leu Pro Leu Ile Gly His Leu
        35                  40                  45

His Leu Leu Trp Gly Lys Leu Pro Gln His Ala Leu Ala Ser Val Ala
    50                  55                  60

Lys Gln Tyr Gly Pro Val Ala His Val Gln Leu Gly Glu Val Phe Ser
65                  70                  75                  80

Val Val Leu Ser Ser Arg Glu Ala Thr Lys Phe Ala Met Lys Leu Val
                85                  90                  95

Asp Pro Ala Cys Ala Asp Arg Phe Glu Ser Ile Gly Thr Lys Ile Met
            100                 105                 110

Trp Tyr Asp Asn Asp Asp Ile Ile Phe Ser Pro Tyr Ser Val His Trp
        115                 120                 125

Arg Gln Met Arg Lys Ile Cys Val Ser Glu Leu Leu Ser Ala Arg Asn
    130                 135                 140

Val Arg Ser Phe Gly Phe Ile Arg Gln Asp Glu Val Ser Arg Leu Leu
145                 150                 155                 160

Gly His Leu Arg Ser Ser Ala Ala Ala Gly Glu Ala Val Asp Leu Thr
                165                 170                 175
```

-continued

```
Glu Arg Ile Ala Thr Leu Thr Cys Ser Ile Cys Arg Ala Ala Phe
            180                 185                 190

Gly Ser Val Ile Arg Asp His Glu Glu Leu Val Glu Leu Val Lys Asp
            195                 200                 205

Ala Leu Ser Met Ala Ser Gly Phe Glu Leu Ala Asp Met Phe Pro Ser
            210                 215                 220

Ser Lys Leu Leu Asn Leu Leu Cys Trp Asn Lys Ser Lys Leu Trp Arg
225                 230                 235                 240

Met Arg Arg Arg Val Asp Ala Ile Leu Glu Ala Ile Val Glu His
                    245                 250                 255

Lys Leu Lys Lys Ser Gly Glu Phe Gly Gly Glu Asp Ile Ile Asp Val
            260                 265                 270

Leu Phe Arg Met Gln Lys Asp Ser Gln Ile Lys Val Pro Ile Thr Ile
            275                 280                 285

Asn Ala Ile Lys Ala Phe Ile Phe Asp Thr Phe Ser Ala Gly Thr Glu
            290                 295                 300

Thr Ser Ser Thr Thr Thr Leu Trp Val Met Ala Glu Leu Met Arg Asn
305                 310                 315                 320

Pro Glu Val Met Ala Lys Ala Gln Ala Glu Val Arg Ala Ala Leu Lys
                    325                 330                 335

Gly Lys Thr Asp Trp Asp Val Asp Val Gln Glu Leu Lys Tyr Met
            340                 345                 350

Lys Ser Val Val Lys Glu Ile Met Arg Met His Pro Pro Ile Pro Leu
            355                 360                 365

Ile Pro Arg Ser Cys Arg Glu Glu Cys Glu Val Asn Gly Tyr Thr Ile
            370                 375                 380

Pro Asn Lys Ala Arg Ile Met Ile Asn Val Trp Ser Met Gly Arg Asn
385                 390                 395                 400

Pro Leu Tyr Trp Glu Lys Pro Gly Thr Phe Trp Pro Glu Arg Phe Asp
                    405                 410                 415

Gln Val Ser Arg Asp Phe Met Gly Asn Asp Phe Glu Phe Ile Pro Phe
            420                 425                 430

Gly Ala Gly Arg Arg Ile Cys Pro Gly Leu Asn Phe Gly Leu Ala Asn
            435                 440                 445

Val Glu Val Pro Leu Ala Gln Leu Leu Tyr His Phe Asp Trp Lys Leu
            450                 455                 460

Ala Glu Gly Met Asn Pro Ser Asp Met Asp Met Ser Glu Ala Glu Gly
465                 470                 475                 480

Leu Thr Gly Ile Arg Lys Asn Asn Leu Leu Leu Val Pro Thr Pro Tyr
                    485                 490                 495

Asp Pro Ser Ser
            500
```

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 3..6
        (D) OTHER INFORMATION: /note= "N-3 and N-6 are Inosine"

```
        (ix) FEATURE:
              (A) NAME/KEY: misc_feature
              (B) LOCATION: 1..14
              (D) OTHER INFORMATION: /product= "Primer 1.AC (Table 1)"

(xi) SEQUENCE DESCRIPTION: SEQ ID NO:10:

GTNWSNAAAR TGMC                                                              14

(2) INFORMATION FOR SEQ ID NO:11:

(i) SEQUENCE CHARACTERISTICS:
              (A) LENGTH: 14 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: misc_feature
              (B) LOCATION: 3..6
              (D) OTHER INFORMATION: /note= "N-3 and N-6 are inosine"

(ix) FEATURE:
              (A) NAME/KEY: misc_feature
              (B) LOCATION: 1..14
              (D) OTHER INFORMATION: /product= "Primer 1.AG (Table 1)"

(xi) SEQUENCE DESCRIPTION: SEQ ID NO:11:

GTNWSNAAAR TGWG                                                              14

(2) INFORMATION FOR SEQ ID NO:12:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: misc_feature
              (B) LOCATION: 6..9
              (D) OTHER INFORMATION: /note= "N-6 and N-9 are inosine"

(ix) FEATURE:
              (A) NAME/KEY: misc_feature
              (B) LOCATION: 1..20
              (D) OTHER INFORMATION: /product= "Primer 1.B (Table 1)"

(xi) SEQUENCE DESCRIPTION: SEQ ID NO:12:

GCYTCNSWNC CYTGRTCYTT                                                        20

(2) INFORMATION FOR SEQ ID NO:13:

(i) SEQUENCE CHARACTERISTICS:
              (A) LENGTH: 29 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: misc_feature
              (B) LOCATION: 6..9
              (D) OTHER INFORMATION: /note= "N-6 and N-9 are inosine"

(ix) FEATURE:
              (A) NAME/KEY: misc_feature
              (B) LOCATION: 1..29
              (D) OTHER INFORMATION: /product= "Primer 1.C (Table 1)"
```

(xi) SEQUENCE DESCRIPTION: SEQ ID NO:13:

GTGTGTCGTC GTGTGCAGGG CGGCGTTCG                                              29

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 9..18
        (D) OTHER INFORMATION: /note= "N-9, N-15 and N-18
            are inosine, guanine or adenine"

(ix) FEATURE:
        (A) NAME/KEY: misc_feature
        (B) LOCATION: 1..19
        (D) OTHER INFORMATION: /product= "Primer 2.AA (Table 1)"

(xi) SEQUENCE DESCRIPTION: SEQ ID NO:14:

ATGGARYTNG AYYTNYTNA                                                         19

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 9..18
        (D) OTHER INFORMATION: /note= "N-9, N-15 and N-18
            are inosine, guanine or adenine"

(ix) FEATURE:
        (A) NAME/KEY: misc_feature
        (B) LOCATION: 1..19
        (D) OTHER INFORMATION: /product= "Primer 2.AT (Table 1)"

(xi) SEQUENCE DESCRIPTION: SEQ ID NO:15:

ATGGARYTNG AYYTNYTNT                                                         19

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 3..15
        (D) OTHER INFORMATION: /note= "N-3, N-9, N-12 and N-15
            are inosine"

(ix) FEATURE:
        (A) NAME/KEY: misc_feature
        (B) LOCATION: 1..17
        (D) OTHER INFORMATION: /product= "Primer 2.B (Table 1)"

(xi) SEQUENCE DESCRIPTION: SEQ ID NO:16:

TCNATRTANG TNGCNAC                                                        17

(2) INFORMATION FOR SEQ ID NO:17:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 9..15
      (D) OTHER INFORMATION: /note= "N-9 and N-15 are inosine"

(ix) FEATURE:
      (A) NAME/KEY: misc_feature
      (B) LOCATION: 1..20
      (D) OTHER INFORMATION: /product= "Primer 3.A (Table 1)"

(xi) SEQUENCE DESCRIPTION: SEQ ID NO:17:

ATGGARGTNA AYGGNTAYAC                                                     20

(2) INFORMATION FOR SEQ ID NO:18:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..19
      (D) OTHER INFORMATION: /product= "Primer 3.B (Table 1)"

(xi) SEQUENCE DESCRIPTION: SEQ ID NO:18:

TTTTTTTTTT TTTTTTTH                                                       19

(2) INFORMATION FOR SEQ ID NO:19:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 6..39
      (D) OTHER INFORMATION: /note= "N-6, N-12, N-18, N-27,
         N-30, N-36 and N-39 are inosine"

(ix) FEATURE:
      (A) NAME/KEY: misc_feature
      (B) LOCATION: 1..41
      (D) OTHER INFORMATION: /product= "Primer 3.C (Table 1)"

(xi) SEQUENCE DESCRIPTION: SEQ ID NO:19:

CCDATNGCDA TNACRTTNAT RAADATNCKN GTYTTNGCNG G                              41

(2) INFORMATION FOR SEQ ID NO:20:

(i) SEQUENCE CHARACTERISTICS:

```
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "Sequencing Primer 22CR3
            (Table 2)"

(xi) SEQUENCE DESCRIPTION: SEQ ID NO:20:

CACGACATCT TCGACACCTC CTCC                                               24

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..22
        (D) OTHER INFORMATION: /product= "Sequencing Primer 22CF1
            (Table 2)"

(xi) SEQUENCE DESCRIPTION: SEQ ID NO:21:

GCAACCTACA TCGTATCCCT CC                                                 22

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "Sequencing Primer NTREV1
            (Table 2)"

(xi) SEQUENCE DESCRIPTION: SEQ ID NO:22:

GGCTCGGAGG TAGGTTTTGT TGGG                                               24

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..27
        (D) OTHER INFORMATION: /product= "Sequencing Primer NTREV2
            (Table 2)"

(xi) SEQUENCE DESCRIPTION: SEQ ID NO:23:

GATTAGGAGG GATACGATGT AGGTTGC                                            27
```

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..22
        (D) OTHER INFORMATION: /product= "Sequencing Primer 11A4.25R6
        (Table 2)"

(xi) SEQUENCE DESCRIPTION: SEQ ID NO:24:

CTGGGCTCAG CAGCTCTGTC AA                                22

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..18
        (D) OTHER INFORMATION: /product= "Sequencing Primer 4.25R5
        (Table 2)"

(xi) SEQUENCE DESCRIPTION: SEQ ID NO:25:

GGGCTCAGCA GCTCTCTC                                    18

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..20
        (D) OTHER INFORMATION: /product= "Sequencing Primer 4.25R3
        (Table 2)"

(xi) SEQUENCE DESCRIPTION: SEQ ID NO:26:

CTTCACCAAC TCCGCCAACG                                  20

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..19
        (D) OTHER INFORMATION: /product= "Sequencing Primer 11A4.25R2

```
            (Table 2)"

(xi) SEQUENCE DESCRIPTION: SEQ ID NO:27:

GCTCTTCTTC TCCCTATGC                                              19

(2) INFORMATION FOR SEQ ID NO:28:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..19
         (D) OTHER INFORMATION: /product= "Sequencing Primer 11A4.25R
             (Table 2)"

(xi) SEQUENCE DESCRIPTION: SEQ ID NO:28:

TAGCTCTTGC ACCTCGCTC                                              19

(2) INFORMATION FOR SEQ ID NO:29:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..25
         (D) OTHER INFORMATION: /product= "Sequencing Primer 11A.1F4
             (Table 2)"

(xi) SEQUENCE DESCRIPTION: SEQ ID NO:29:

TTCGGGAGTG TGCTCAAGGA CCAGG                                       25

(2) INFORMATION FOR SEQ ID NO:30:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..20
         (D) OTHER INFORMATION: /product= "Sequencing Primer 11A1F3
             (Table 2)"

(xi) SEQUENCE DESCRIPTION: SEQ ID NO:30:

GTTGGTGAAG GAGTTCGCTG                                             20

(2) INFORMATION FOR SEQ ID NO:31:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: cDNA
```

(ix) FEATURE:
         (A) NAME/KEY: misc_feature
         (B) LOCATION: 1..17
         (D) OTHER INFORMATION: /product= "Sequencing Primer 11A.1F2
             (Table 2)"

(xi) SEQUENCE DESCRIPTION: SEQ ID NO:31:

CTTACAACGA TCACTGG                                                    17

(2) INFORMATION FOR SEQ ID NO:32:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..24
         (D) OTHER INFORMATION: /product= "Sequencing Primer S12.2PF1
             (Table 2)"

(xi) SEQUENCE DESCRIPTION: SEQ ID NO:32:

GACATCGTCG ACGTTCTTTT CAGG                                            24

(2) INFORMATION FOR SEQ ID NO:33:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..23
         (D) OTHER INFORMATION: /product= "Sequencing Primer S12.2PF2
             (Table 2)"

(xi) SEQUENCE DESCRIPTION: SEQ ID NO:33:

CTACCACTTC GACTGGAAAT TGC                                             23

(2) INFORMATION FOR SEQ ID NO:34:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..23
         (D) OTHER INFORMATION: /product= "Sequencing Primer S12.2PF3
             (Table 2)"

(xi) SEQUENCE DESCRIPTION: SEQ ID NO:34:

CTGAGATCGG TGTTAAAGGA GAC                                             23

(2) INFORMATION FOR SEQ ID NO:35:

(i) SEQUENCE CHARACTERISTICS:
         (A) LENGTH: 23 base pairs

```
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..23
            (D) OTHER INFORMATION: /product= "Sequencing Primer S12.2PR1
                (Table 2)"

(xi) SEQUENCE DESCRIPTION: SEQ ID NO:35:

GCCACCTCTA TAAGACACTC CTC                                              23

(2) INFORMATION FOR SEQ ID NO:36:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..19
            (D) OTHER INFORMATION: /product= "Sequencing Primer S12.2PR2
                (Table 2)"

(xi) SEQUENCE DESCRIPTION: SEQ ID NO:36:

GATCTCAACA TTTGCCAGC                                                   19

(2) INFORMATION FOR SEQ ID NO:37:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..19
            (D) OTHER INFORMATION: /product= "Sequencing Primer S12BF
                (Table 2)"

(xi) SEQUENCE DESCRIPTION: SEQ ID NO:37:

GAAACCATGG AGCTCGACC                                                   19

(2) INFORMATION FOR SEQ ID NO:38:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..19
            (D) OTHER INFORMATION: /product= "Sequencing Primer S17.1F2
                (Table 2)"

(xi) SEQUENCE DESCRIPTION: SEQ ID NO:38:

CGACGACATC ATCTTCAGC                                                   19
```

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "Sequencing Primer S17F1
        (Table 2)"

(xi) SEQUENCE DESCRIPTION: SEQ ID NO:39:

AGTACGGTCC AGTGGTGCAC GTGC                                        24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "Sequencing Primer S17.1.2F3
        (Table 2)"

(xi) SEQUENCE DESCRIPTION: SEQ ID NO:40:

GAGGAGCTGG TGGAGCTGGT GAAG                                        24

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..23
        (D) OTHER INFORMATION: /product= "Sequencing Primer S17.1.2F5
        (Table 2)"

(xi) SEQUENCE DESCRIPTION: SEQ ID NO:41:

CGAGATCATG CAGAGAAGAA TGC                                         23

(2) INFORMATION FOR SEQ ID NO:42:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..23
        (D) OTHER INFORMATION: /product= "Sequencing Primer P17R1
        (Table 2)"

```
    (xi) SEQUENCE DESCRIPTION: SEQ ID NO:42:

ATGGGACCTC AACATTTGGC AAC                                                    23

(2) INFORMATION FOR SEQ ID NO:43:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..19
        (D) OTHER INFORMATION: /product= "Sequencing Primer P17.1R2
        (Table 2)"

(xi) SEQUENCE DESCRIPTION: SEQ ID NO:43:

ATGTTCTTGG CCTTATTCG                                                         19

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..25
        (D) OTHER INFORMATION: /product= "Sequencing Primer P17.1.2R4
        (Table 2)"

(xi) SEQUENCE DESCRIPTION: SEQ ID NO:44:

CAGAGCAAGT TGAGGAGCTT GGAGG                                                  25

(2) INFORMATION FOR SEQ ID NO:45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..25
        (D) OTHER INFORMATION: /product= "Sequencing Primer P17.1.2F4
        (Table 2)"

(xi) SEQUENCE DESCRIPTION: SEQ ID NO:45:

CCATCACCAC CAACGCCATC AAAGC                                                  25

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA
```

```
    (ix) FEATURE:
         (A) NAME/KEY: misc_feature
         (B) LOCATION: 1..20
         (D) OTHER INFORMATION: /product= "Sequencing Primer P17.1.2R6
             (Table 2)"

(xi) SEQUENCE DESCRIPTION: SEQ ID NO:46:

GTACTGCTTC GCCACGCTGG                                                    20

(2) INFORMATION FOR SEQ ID NO:47:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..25
         (D) OTHER INFORMATION: /product= "Sequencing Primer BLUT3
             (Table 2)"

(xi) SEQUENCE DESCRIPTION: SEQ ID NO:47:

CGCGCAATTA ACCCTCACTA AAGGG                                              25

(2) INFORMATION FOR SEQ ID NO:48:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..16
         (D) OTHER INFORMATION: /product= "Sequencing Primer 11A4.10F
             (Table 2)"

(xi) SEQUENCE DESCRIPTION: SEQ ID NO:48:

GCTGAATGGG CAATGG                                                        16

(2) INFORMATION FOR SEQ ID NO:49:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: misc_feature
         (B) LOCATION: 1..18
         (D) OTHER INFORMATION: /product= "Sequencing Primer 11A.1F-A
             (Table 2)"

(xi) SEQUENCE DESCRIPTION: SEQ ID NO:49:

CACCTCCACT TCCTGTGG                                                      18

(2) INFORMATION FOR SEQ ID NO:50:

(i) SEQUENCE CHARACTERISTICS:
         (A) LENGTH: 25 base pairs
         (B) TYPE: nucleic acid
```

```
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..25
        (D) OTHER INFORMATION: /product= "Sequencing Primer P17.1.2R5
            (Table 2)"

(xi) SEQUENCE DESCRIPTION: SEQ ID NO:50:

GCTGAAGAGC TCGGAGACGC AGATC                                             25

(2) INFORMATION FOR SEQ ID NO:51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..18
        (D) OTHER INFORMATION: /product= "PCR Primer P17START
            (Table 3)"

(xi) SEQUENCE DESCRIPTION: SEQ ID NO:51:

ATGGAGCTTC AGATTTCG                                                     18

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..21
        (D) OTHER INFORMATION: /product= "PCR Primer P17RSTOP
            (Table 3)"

(xi) SEQUENCE DESCRIPTION: SEQ ID NO:52:

GCACTCTTTA TTCAAAGGAG C                                                 21

(2) INFORMATION FOR SEQ ID NO:53:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..19
        (D) OTHER INFORMATION: /product= "PCR Primer S12BF
            (Table 3)"

(xi) SEQUENCE DESCRIPTION: SEQ ID NO:53:

GAAACCATGG AGCTCGACC                                                    19
```

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..20
        (D) OTHER INFORMATION: /product= "PCR Primer S12BR
        (Table 3)"

(xi) SEQUENCE DESCRIPTION: SEQ ID NO:54:

TATGCTAAGC TTCTTAGTGG                                                    20

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "PCR Primer BAC4PCR-F
        (Table 3)"

(xi) SEQUENCE DESCRIPTION: SEQ ID NO:55:

TTTACTGTTT TCGTAACAGT TTTG                                               24

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..21
        (D) OTHER INFORMATION: /product= "PCR Primer BAC4PCR-R
        (Table 3)"

(xi) SEQUENCE DESCRIPTION: SEQ ID NO:56:

CAACAACGCA CAGAATCTAG C                                                  21

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "PCR Primer BAC3PCR-F
        (Table 3)"

-continued

```
    (xi) SEQUENCE DESCRIPTION: SEQ ID NO:57:

TTTACTGTTT TCGTAACAGT TTTG                                              24

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..21
        (D) OTHER INFORMATION: /product= "PCR Primer BAC3PCR-R
            (Table 3)"

(xi) SEQUENCE DESCRIPTION: SEQ ID NO:58:

CAACAACGCA CAGAATCTAG C                                                 21
```

RECOMBINANT MATERIALS AND METHODS FOR THE PRODUCTION OF LIMONENE HYDROXYLASES

This invention was supported in part by grant number MCB 96-04918 awarded by the National Science Foundation. The government has certain rights in the invention.

FIELD OF THE INVENTION

The present invention relates to nucleic acid sequences which code for cytochrome P450 limonene hydroxylases, such as (−)-limonene-6-hydroxylase from *Mentha spicata* and (−)-limonene-3-hydroxylase from *Mentha piperita*, and to vectors containing the sequences, host cells containing the sequences and methods of producing recombinant limonene hydroxylases and their mutants.

BACKGROUND OF THE INVENTION

Several hundred naturally occurring, monoterpenes are known, and essentially all are biosynthesized from geranyl pyrophosphate, the ubiquitous $C_{10}$ intermediate of the isoprenoid pathway (Croteau and Cane, *Methods of Enzymology* 110:383–405 [1985]; Croteau, *Chem. Rev.* 87:929–954 [1987]). Monoterpene synthases, often referred to as "cyclases," catalyze the reactions by which geranyl pyrophosphate is cyclized to the various monoterpene carbon skeletons. Many of the resulting carbon skeletons undergo subsequent oxygenation by cytochrome P450 hydroxylases to give rise to large families of derivatives. Research on biosynthesis has been stimulated by the commercial significance of the essential oils (Guenther, *The Essential Oils*, Vols. III–VI (reprinted) R. E. Krieger, Huntington, N.Y. [1972]) and aromatic resins (Zinkel and Russell, *Naval Stores: Production, Chemistry, Utilization*, Pulp Chemicals Association, New York [1989]) and by the ecological roles of these terpenoid secretions, especially in plant defense (Gershenzon and Croteau, in "Herbivores: Their Interactions with Secondary Plant Metabolites," Vol. I, 2nd Ed. (Rosenthal and Berenbaum, eds.) Academic Press, San Diego, Calif., pp. 165–219 [1991]; Harborne, in "Ecological Chemistry and Biochemistry of Plant Terpenoids," (Harborne and Tomas-Barberan, eds.) Clarendon Press, Oxford, Mass., pp. 399–426 [1991]).

The reactions catalyzed by the cytochrome P450-(−)-limonene hydroxylases determine the oxidation pattern of the monoterpenes derived from limonene (see FIGS. 1A–1C). These reactions are completely regiospecific and are highly selective for (−)-limonene as substrate. The primary products of limonene hydroxylation (trans-carveol and trans-isopiperitenol) are important essential oil components and serve as precursors of numerous other monoterpenes of flavor or aroma significance (see FIGS. 1A–1C).

One of the major classes of plant monoterpenes is the monocyclic p-menthane (1-methyl-4-isopropylcyclohexane) type, found in abundance in members of the mint (Mentha) family. The biosynthesis of p-menthane monoterpenes in Mentha species, including the characteristic components of the essential oil of peppermint (i.e., (−)-menthol) and the essential oil of spearmint (i.e., (−)-carvone), proceeds from geranyl pyrophosphate via the cyclic olefin (−)-limonene and is followed by a series of enzymatic redox reactions that are initiated by cytochrome P450 limonene hydroxylases (e.g., limonene-3-hydroxylase in peppermint and limonene-6-hydroxylase in spearmint and related species; Karp et al., *Arch. Biochem. Biophys.* 276:219–226 [1990]; Gershenzon et al., *Rec. Adv. Phytochem.* 28:193–229 [1994]; Lupien et al., *Drug Metab. Drug Interact.* 12:245–260 [1995]. The products of limonene hydroxylation and their subsequent metabolites also serve ecological roles in plant defense mechanisms against herbivores and pathogens, and may act as signals in other plant-insect relationships (e.g., as attractants for pollinators and seed dispersers) as shown in FIGS. 1A–1C.

A detailed understanding of the control of monoterpene biosynthesis and of the reaction mechanisms, enzymes and the relevant cDNA clones as tools for evaluating patterns of developmental and environmental regulation, for examining active site structure function relationships and for the generation of transgenic organisms bearing such genes are disclosed in part in parent U.S. related application Ser. No. 08/582,802 filed Jan. 4, 1996 as a continuation of application Ser. No. 08/145,941 filed Oct. 28, 1993, the disclosures of which are incorporated herein by this reference, which disclose the isolation and sequencing of cDNAs encoding (−)4S-limonene synthase, the enzyme responsible for cyclizing geranyl pyrophosphate to obtain (−)-limonene. To date, however, no information has been available in the art regarding the protein and nucleotide sequences relating to the enzymes through which (−)-limonene is hydroxylated (by the action of (−)-limonene-6-hydroxylase to form trans-carveol or by the action of (−)-limonene-3-hydroxylase to form trans-isopiperitenol as shown in FIG. 1).

SUMMARY OF THE INVENTION

In accordance with the foregoing, cDNAs encoding (−)-limonene hydroxylase, particularly (−)-limonene-6-hydroxylase from spearmint and (−)-limonene-3-hydroxylase from peppermint, have been isolated and sequenced, and the corresponding amino acid sequences have been deduced. Accordingly, the present invention relates to isolated DNA sequences which code for the expression of limonene hydroxylase, such as the sequence designated SEQ ID No:1 which encodes (−)-limonene-6-hydroxylase from spearmint (*Mentha spicata*) or the sequence designated SEQ ID No:3 which encodes (−)-limonene-3-hydroxylase from peppermint (*Mentha piperita*). In other aspects, the present invention is directed to replicable recombinant cloning vehicles comprising a nucleic acid sequence, e.g., a DNA sequence, which codes for limonene hydroxylases or for a base sequence sufficiently complementary to at least a portion of the limonene hydroxylase DNA or RNA to enable hybridization therewith (e.g., antisense limonene hydroxylase RNA or fragments of complementary limonene hydroxylase DNA which are useful as polymerase chain reaction primers or as probes for limonene hydroxylases or related genes). In yet other aspects of the invention, modified host cells are provided that have been transformed, transfected, infected and/or injected with a recombinant cloning vehicle and/or DNA sequence of the invention. Thus, the present invention provides for the recombinant expression of limonene hydroxylases, and the inventive concepts may be used to facilitate the production, isolation and purification of significant quantities of recombinant limonene hydroxylase (or of the primary enzyme products, trans-carveol in the case of (−)-limonene-6-hydroxylase or trans-isopiperitenol in the case of (−)-limonene-3-hydroxylase) for subsequent use, to obtain expression or enhanced expression of limonene hydroxylase in plants to attain enhanced trans-carveol or trans-isopiperitenol production as a predator or pathogen defense mechanism, attractant or environmental signal, or may be otherwise employed in an environment where the regulation or expression of limonene hydroxylase is desired for the production of limonene hydroxylase or the enzyme products, trans-carveol or trans-isopiperitenol, or their derivatives.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

As shown in FIG. 1A, after geranyl pyrophosphate is cyclized to limonene, the limonene is acted on by (−)-limonene-6-hydroxylase (L6-OH in FIG. 1A) to form trans-carveol or by (−)-limonene-3-hydroxylase (L3-OH in FIG. 1A) to form trans-isopiperitenol. Subsequently, as shown in FIGS. 1B and 1C, a series of secondary redox transformations convert these olefinic intermediates to other monoterpenes;

FIG. 2 shows the monoterpene olefins, in addition to (−)-limonene, (i.e., (+)-limonene, (−)-p-menth-1-ene, and (+)-p-menth-1-ene) shown to be limonene-6-hydroxlase and limonene-3-hydroxlase substrates, and the percentage conversion to products as compared to the conversion of (−)-limonene at saturation;

FIG. 3 shows the amino acid sequence (SEQ ID No:1) encoded by plasmid pSM 12 that encodes (−)-limonene-6-hydroxylase from *Mentha spicata* derived as described in Examples 1–3. The V-8 proteolytic fragments V-8.1, V-8.2 and V-8.3, generated as described in Example 3 are shown in brackets, and amino acid sequence data generated from the amino-terminal sequence analysis of V-8.1(SEQ ID No:2), V-8.2 (SEQ ID No:3), and V-8.3 (SEQ ID No:4) are underlined. FIG. 3 also shows the membrane insertion sequence at amino acids 7–48 (SEQ ID No:1, location 7 . . . 48), the halt-transfer signal at 44–48 (SEQ ID No:1, location 44 . . . 48) and the heme binding region at 429–454 (SEQ ID No:1, location 429 . . . 454);

FIG. 4 shows the nucleotide sequence (SEQ ID No:5) of (−)-limonene-6-hydroxylase cDNA derived as described in Example 5. The sequences of cDNA probes LH-1 (SEQ ID No:6) and LH-2 (SEQ ID No:7) as described in Examples 4 and 5, respectively, are underlined;

FIG. 5 shows the nucleotide sequence (SEQ ID No:8) of peppermint limonene hydroxylase clone pPM17 derived from *Mentha piperita* as described in Example 5;

FIG. 6 shows the predicted amino acid sequence (SEQ ID No:9) of peppermint limonene hydroxylase as derived from the nucleotide squence of clone pPM17 (SEQ ID No:8) as described in Example 5; and FIG. 7 shows an amino acid comparison of (−)-limonene-6-hydroxylase from *Mentha spicata* (SEQ ID No:1) encoded by plasmid pSM12 with the predicted amino acid sequence (SEQ ID No:9) of peppermint limonene hydroxylase from *Mentha piperita* derived from the nucleotide squence of clone pPM17.

DETAILED DESCRIPTION OF THE PREFERRED EMBODIMENT

Figure 1A:
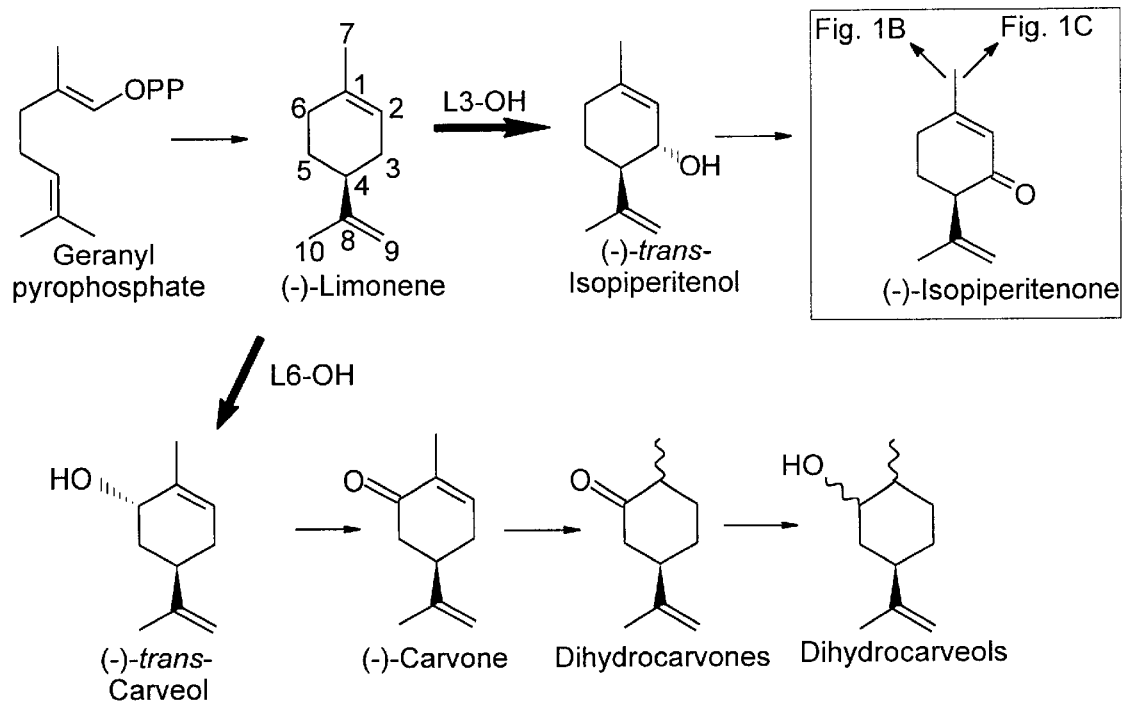
FIGS. 1A–1C are schematic representations of the principal pathways of monoterpene biosynthesis in spearmint leading to carvone and in peppermint leading to menthol.
Figure 1B:
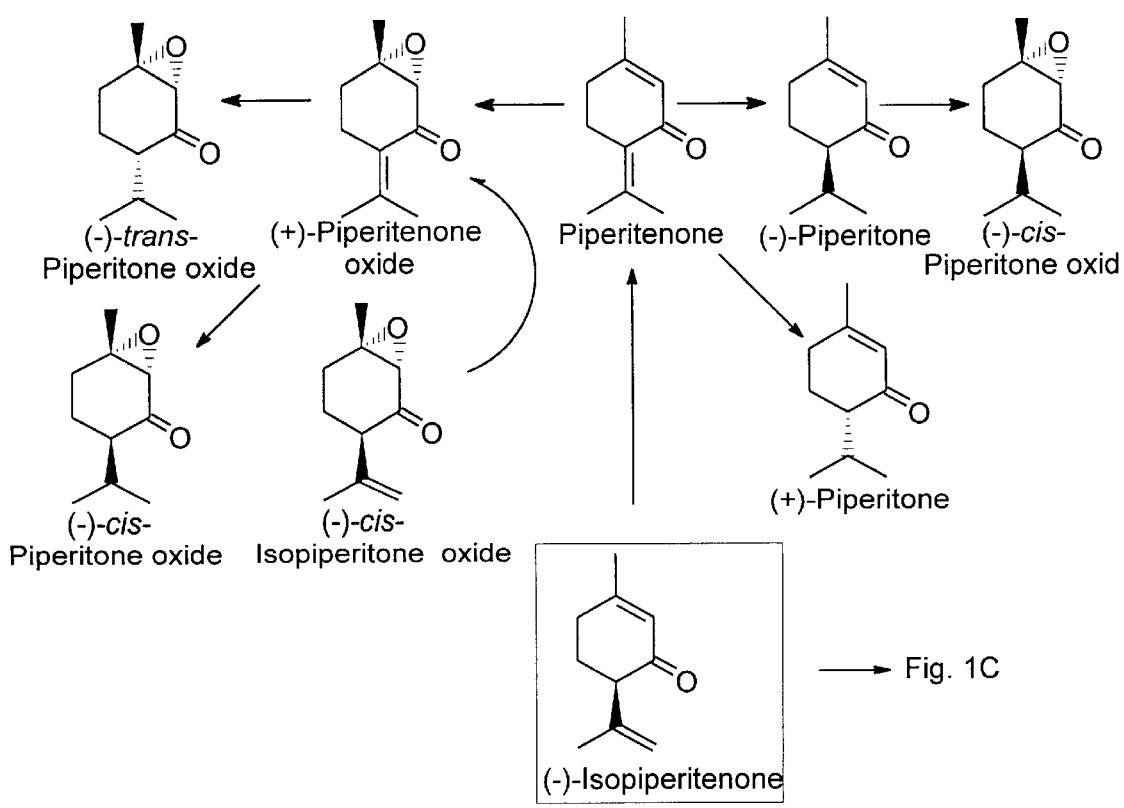
Figure 1C:
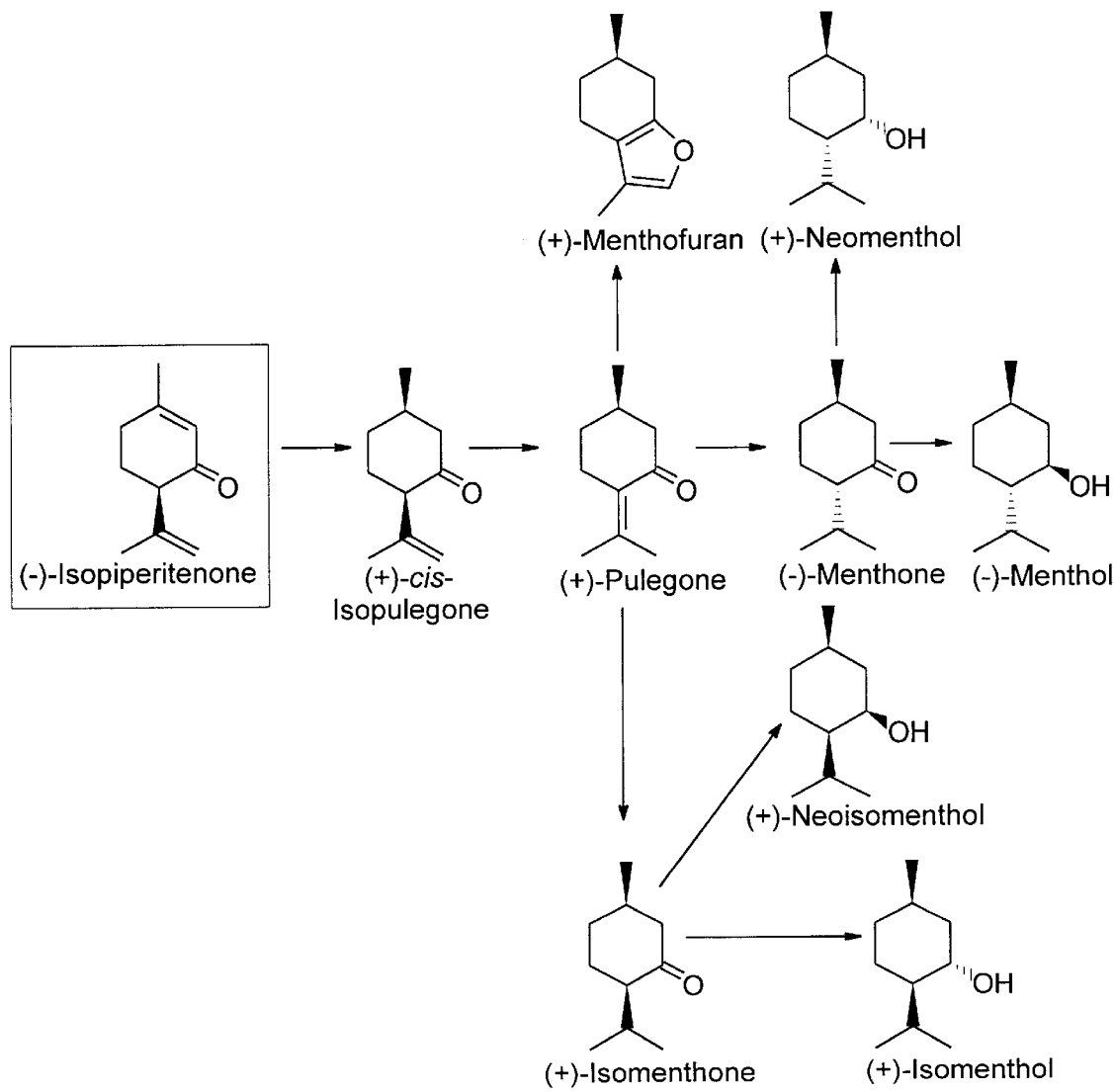

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nueleoside. The base characterizes the nucleotide with the four bases of DNA being adenine ("A"), guanine ("G"), cytosine ("C"), thymine ("T") and inosine ("I"). The four RNA bases are A,G,C and uracil ("U"). The nucleotide sequences described herein comprise a line array of nucleotides connected by phosphodiester bonds between the 3' and 5' carbons of adjacent pentoses.

"Oligonucleotide" refers to short length single or double stranded sequences of deoxyribonucleotides linked via phosphodiester bonds. The oligonucleotides are chemically synthesized by known methods and purified on polyacrylamide gels.

The term "limonene hydroxylase" is used herein to mean an enzyme capable of catalyzing the hydroxylation of limonene to its hydroxylated products, such as trans-carveol in the case of (−)-limonene-6-hydroxylase or trans-isopiperitenol in the case of (−)-limonene-3-hydroxylase, as described herein.

The terms "alteration", "amino acid sequence alteration", "variant" and "amino acid sequence variant" refer to limonene hydroxylase molecules with some differences in their amino acid sequences as compared to native limonene hydroxylase. Ordinarily, the variants will possess at least about 70% homology with native limonene hydroxylase, and preferably, they will be at least about 80% homologous with native limonene hydroxylase. The amino acid sequence variants of limonene hydroxylase falling within this invention possess substitutions, deletions, and/or insertions at certain positions. Sequence variants of limonene hydroxylase may be used to attain desired enhanced or reduced enzymatic activity, modified regiochemistry or stereochemistry, or altered substrate utilization or product distribution such as enhanced production of other products obtained from alternative substrates, such as those shown in FIG. 2.

Substitutional limonene hydroxylase variants are those that have at least one amino acid residue in the native limonene hydroxylase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the limonene hydroxylase molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the limonene hydroxylase molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional limonene hydroxylase variants are those with one or more amino acids inserted immediately adjacent to an amino acid at a particular position in the native limonene hydroxylase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native limonene hydroxylase molecule have been removed. Ordinarily, deletional variants will have one or two amino acids deleted in a particular region of the limonene hydroxylase molecule.

The terms "biological activity", "biologically active", "activity" and "active" refer to the ability of the limonene hydroxylase molecule to convert (−)-limonene to carveol and isopiperitenol and co-products as measured in an enzyme activity assay, such as the assay described in Example 7 below. Amino acid sequence variants of limonene hydroxylase may have desirable altered biological activity including, for example, altered reaction kinetics, substrate utilization product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell" and "transformed" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

In accordance with the present invention, cDNA encoding limonene hydroxylase was isolated and sequenced in the following manner. (−)-Limonene hydroxylase is located exclusively in the glandular trichome secretory cells and catalyzes the hydroxylation of (−)-limonene in these essential oil species. Known methods for selectively isolating secretory cell clusters from these epidermal oil glands and for extracting these structures were employed to obtain sufficient amounts of light membranes (microsomes). The light membranes were solubilized and the resulting protein subjected to hydrophobic interaction chromatography which served to purify a spectrally characterized (Omura et al., *J. Biol. Chem.* 239:2379–2385 [1964]) cytochrome P450 enzyme from spearmint secretory glands. This approach, however, does not differentiate between enzymatically distinct cytochrome P450 species. Amino acid sequence information derived from the purified protein was employed in a molecular approach to the isolation of gland specific cDNA clones encoding such cytochromes. Following isolation and sequencing of the cytochrome P450 cDNA (pSM12.2, SEQ ID No:5, FIG. 4) from spearmint, functional expression was required to confirm the catalytic identity of the enzyme encoded. A Spodoptera-Baculovirus expression system, combined with the in situ bioassay (feeding (−)-limonene substrate during recombinant protein expression), successfully confirmed that the target clone (limonene-6-hydroxylase) had been isolated. Sequence information from the full length spearmint limonene hydroxylase cDNA was utilized to construct a selective probe for the isolation of the related (−)-limonene-3-hydroxylase gene (pPM17, SEQ ID No:8, FIG. 5) from peppermint secretory glands. Functional expression in the Spodoptera-Baculovirus expression system, by in situ bioassay, also confirmed the peppermint limonene-3-hydroxylase clone, which was fully sequenced. Sequence comparison showed the two regiospecific hydroxylases from spearmint and peppermint to be very similar (see FIG. 7), as expected, since spearmint (*M. spicata*) is a tetraploid and parent of peppermint (*M. piperita=Mentha aquatica*×spicata), a hexaploid (Harley and Brighton, *Bot. J. Linn. Soc.* 74:71–96 [1977]). In vitro studies confirmed the recombinant enzymes to resemble their native counterparts.

The isolation of the limonene hydroxylase cDNA permits the development of an efficient expression system for this functional enzyme with which such detailed mechanistic structural studies can be undertaken. The limonene hydroxylase cDNA also provides a useful tool for isolating other monoterpene hydroxylase genes and for examining the developmental regulation of monoterpene biosynthesis.

Although the limonene hydroxylase cDNA set forth in SEQ ID No:5 directs the enzyme to plastids, substitution of the targeting sequence (SEQ ID No:5, nucleotides 20 to 146) with other transport sequences well known in the art (see, e.g., Keegstra et al., supra; von Heijne et al., supra) may be employed to direct the limonene hydroxylase to other cellular or extracellular locations.

In addition to the native (−)-limonene-6-hydroxylase amino acid sequence of SEQ ID No:1 encoded by the DNA sequence of pSM 12.2 (SEQ ID No:5) and the native (−)-limonene-3-hydroxylase amino acid sequence of SEQ ID No:9 encoded by the DNA sequence of pPM 17 (SEQ ID No:8), sequence variants produced by deletions, substitutions, mutations and/or insertions are intended to be within the scope of the invention except insofar as limited by the prior art. The limonene hydroxylase amino acid sequence variants of this invention may be constructed by mutating the DNA sequence that encodes wild-type limonene hydroxylase, such as by using techniques commonly referred to as site-directed mutagenesis. Various polymerase chain reaction (PCR) methods now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of E. coli. Plasmid DNA is isolated from the transformed bacteria, restricted with the relevant restriction enzyme (thereby linearizing the unrmutated plasmids), and then retransformed into E. coli. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

In the case of the hydrophobic cleft of the hydroxylases, a number of residues may be mutagenized in this region. Directed mutagenesis can also be used to create cassettes for saturation mutagenesis. Once a hydrophobic segment of the active site is identified, oligonucleotide-directed mutagenesis can be used to create unique restriction sites flanking that region to allow for the removal of the cassette and the subsequent replacement with synthetic cassettes containing any number of mutations within. This approach can be carried out with any plasmid, without need for subcloning or generation of single-stranded phagemids.

The verified mutant duplexes in the pET (or other) overexpression vector can be employed to transform E. coli such as strain E. coli BL21(DE3)pLysS, for high level production of the mutant protein, and purification by metal ion affinity chromatography and thrombin proteolysis. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutagenesis, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native cyclase. If the residue is by this means demonstrated to be important by activity impairment, or knockout, then conservative substitutions can be made, such as Asp for Glu to alter side chain length, Ser for Cys, or Arg for His. For hydrophobic segments, it is largely size that we will alter, although aromatics can also be substituted for alkyl side chains. Changes in the normal product distribution can indicate which step(s) of the reaction sequence have been altered by the mutation. Modification of the hydrophobic pocket can be employed to change binding conformations for substrates and result in altered regiochemistry and/or stereochemistry.

Other site directed mutagenesis techniques may also be employed with the nucleotide sequences of the invention. For example, restriction endonuclease digestion of DNA followed by ligation may be used to generate limonene hydroxylase deletion variants, as described in section 15.3 of Sambrook et al. (*Molecular Cloning: A Laboratory Manual*, 2nd Ed., Cold Spring Harbor Laboratory Press, New York, N.Y. [1989]). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 [1983]). Generally, oligonucleotides of at least 25 nucleotides in length are used to insert, delete or substitute two or more nucleotides in the limonene hydroxylase molecule. An optimal oligonucleotide will have 12 to 15 perfectly matched nucleotides on either side of the nucleotides coding for the mutation. To mutagenize the wild-type limonene hydroxylase, the oligonucleotide is annealed to the single-stranded DNA template molecule under suitable hybridization conditions. A DNA polymerizing enzyme, usually the Klenow fragment of E. coli DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type limonene hydroxylase inserted in the vector, and the second strand of DNA encodes the mutated form of limonene hydroxylase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type limonene hydroxylase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

The genes encoding the (−)-limonene hydroxylase enzymes may be incorporated into any organism (intact plant, animal, microbe or cell culture, etc.) that produces limonene (either as a native property or via transgenic manipulation of limonene synthase) to affect the conversion of limonene to carveol or isopiperitenol (and their subsequent metabolites, depending on the organism) to produce or modify the flavor and aroma properties, to improve defense capability, or to alter other ecological interactions mediated by these metabolites or for the production of the metabolites themselves. The expressed hydroxylases may also be used outside of living cells as a reagent to catalyze the corresponding oxidations of limonene in vitro. Since (+)-limonene also serves as a substrate for these hydroxylases (albeit less efficiently, see FIG. 2), the methods and recombinant enzymes of the present invention are useful for the production of all stereoisomeric products derived by either C3- or C6-hydroxlyation of (+)- or (−)-limonene or related compounds.

Eukaryotic expression systems are commonly employed for cytochrome P450 expression since they carry out any required posttranslational modifications, direct the enzyme to the proper membrane location, and possess a compatible reductase to deliver electrons to the cytochrome. A representative eucaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Biotechnology* 6:47–55 [1987]) for expression of the limonene hydroxylases of the invention. Infection of insect cells (such as cells of the species *Spodoptera frugiperda*) with the recombinant baculoviruses allows for the production of large amounts of the limonene hydroxylase protein. In addition, the baculovirus system has other important advantages for the production of recombinant limonene hydroxylase. For example, baculoviruses do not infect humans and can therefore be safely handled in large quantities. In the baculovirus system, a DNA construct is prepared including a DNA segment encoding limonene hydroxylase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/limonene hydroxylase combination is flanked on both sides by 200–300 base pairs of baculovirus DNA (the flanking sequences).

To produce the limonene hydroxylase DNA construct, a cDNA clone encoding the full length limonene hydroxylase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full limonene hydroxylase. For example, an insect host cell can be cotransfected or transfected separately with the DNA construct and a functional baculovirus. Resulting recombinant baculoviruses can then be isolated and used to infect cells to effect production of the limonene hydroxylase. Host insect cells include, for example, *Spodoptera frugiperda* cells, that are capable of producing a baculovirus-expressed limonene hydroxylase. Insect host cells infected with a recombinant baculovirus of the present invention are then cultured under conditions allowing expression of the baculovirus-encoded limonene hydroxylase. Limonene hydroxylase thus produced is then extracted from the cells using methods known in the art. For a detailed description of the use of the baculovirus/Spodoptera expression system, see Examples 5 and 6, infra.

Other eukaryotic microbes such as yeasts may also be used to practice this invention. The baker's yeast Saccharomyces cerevisiae, is a commonly used yeast, although several other strains are available. The plasmid YRp7 (Stinchcomb et al., *Nature* 282:39 [1979]; Kingsman et al., *Gene* 7:141 [1979]; Tschemper et al., *Gene* 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 [1978].

Suitable promoting sequences in yeast vectors include the promoters for 3-phosphoglycerate kinase (Hitzeman et al., *J. Biol. Chem.* 255:2073 [1980]) or other glycolytic enzymes (Hess et al., *J. Adv. Enzyme Reg.* 7:149 [1968]; Holland et al., *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms and multicellular organisms, such as plants, may be used as hosts to practice this invention. For example, transgenic plants can be obtained such as by transferring plasmids that encode limonene hydroxylase and a selectable marker gene, e.g., the kan gene encoding resistance to kanamycin, into *Agrobacterium tumifaciens* containing a helper Ti plasmid as described in Hoeckema et al., *Nature* 303:179–181 [1983] and culturing the Agrobacterium cells with leaf slices of the plant to be transformed as described by An et al., *Plant Physiology* 81:301–305 [1986]. Transformation of cultured plant host cells is normally accomplished through *Agrobacterium tumifaciens*, as described above. Cultures of mammalian host cells and other host cells that do not have rigid cell membrane barriers are usually transformed using the calcium phosphate method as originally described by Graham and Van der Eb (*Virology* 52:546 [1978]) and modified as described in sections 16.32–16.37 of Sambrook et al., supra. However, other methods for introducing DNA into cells such as Polybrene (Kawai and Nishizawa, *Mol. Cell. Biol.* 4:1172 [1984]), protoplast fusion (Schaffner, *Proc. Natl. Acad. Sci. USA* 77:2163 [1980]), electroporation (Neumann et al., *EMBO J.* 1:841 [1982]), and direct microinjection into nuclei (Capecchi, *Cell* 22:479 [1980]) may also be used. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating limonene hydroxylase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced (nor is the corresponding hydroxylation product of limonene).

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a limonene hydroxylase gene that previously has had its native promoter removed. This engineered gene is the combination of a promoter that responds to an external chemical stimulus and a gene responsible for successful production of limonene hydroxylase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. [1993]). Representative examples include electroporation-facilitated DNA uptake by protoplasts (Rhodes et al., *Science* 240(4849):204–207 [1988]); treatment of protoplasts with polyethylene glycol (Lyznik et al., *Plant Molecular Biology* 13:151–161 [1989]); and bombardment of cells with DNA laden microprojectiles (Klein et al., *Plant Physiol.* 91:440–444 [1989] and Boynton et al., *Science* 240(4858):1534–1538 [1988]); all incorporated by reference. Minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Another screenable gene is a transcriptional activator for anthocyanin biosynthesis, as described in the copending application of Bowen et al., U.S. patent application serial No. 387,739, filed Aug. 1, 1989. This gene causes the synthesis of the pigment anthocyanin. Cells transformed with a plasmid containing this gene turn red. Preferably, the plasmid will contain both selectable and screenable marker genes.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.* 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 [1980]); and TRI cells (Mather et al., *Annals N.Y. Acad. Sci.* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 [1978]). Smaller or larger SV40 DNA fragments may also used, provided they contain the approximately 250-bp sequence extending from the HindIII site toward the BgII site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

Satisfactory amounts of limonene hydroxylase are produced by transformed cell cultures. However, the use of a secondary DNA coding sequence can enhance production levels. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC No. 31,446), *E. coli* strain W3110 (ATCC No.27,325) *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells.

As a representative example, cDNA sequences encoding limonene hydroxylase may be transferred to the $(His)_6$.Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein within thrombin, and the limonene hydroxylase again purified by immobilized metal ion affinity chromatography, this time using a shallower imidazole gradient to elute the recombinant hydroxylase while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl. Acids Res.* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W.H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.* 11:1657 [1983]), alpha-factor, alkaline phosphatase and invertase may be used to direct secretion from yeast host cells. Prokaryotic signal sequences from genes encoding, for example, LamB or OmpF (Wong et al., *Gene* 68:193 [1988]), MalE, PhoA, or beta-lactamase, as well as other genes, may be used to target proteins from prokaryotic cells into the culture medium.

As described above, the limonene hydroxylase amino terminal membrane insertion sequence resides at SEQ ID No:1, residues 1 through 42, and in the embodiment shown in SEQ ID No:1 directs the enzyme to endoplasmic reticulum membranes. Alternative trafficking sequences from plants, animals and microbes can be employed in the practice of the invention to direct the gene product to the cytoplasm, plastids, mitochondria or other cellular components, or to target the protein for export to the medium. These considerations apply to the overexpression of (−)-limonene-6-hydroxylase or (−)-limonene-3-hydroxylase, and to direction of expression within cells or intact organisms to permit gene product function in any desired location.

The construction of suitable vectors containing DNA encoding replication sequences, regulatory sequences, phenotypic selection genes and the limonene hydroxylase DNA of interest are prepared using standard recombinant DNA procedures. Isolated plasmids and DNA fragments are cleaved, tailored, and ligated together in a specific order to generate the desired vectors, as is well known in the art (see, for example, Maniatis, supra), and Sambrook et al., supra).

As discussed above, limonene hydroxylase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60-1.61 and sections 3.38-3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 [1982]), and Goeddel et al. (*Nucleic Acids Res.*, supra).

The following examples merely illustrate the best mode now contemplated for practicing the invention, but should not be construed to limit the invention. All literature citations herein are expressly incorporated by reference.

EXAMPLES

Example 1

Plant Material and Limonene-6-Hydroxylase Isolation

Plant materials—Spearmint (*Mentha spicata*) plants were propagated from rhizomes or stem cuttings in peat moss:pumice:sand (58:35:10, v/v/v) and were grown in a greenhouse with supplemental lighting (16 h, 21,000 lux minimum) and a 30°/15° C. (day/night) temperature cycle. Plants were watered as needed and fertilized daily with a complete fertilizer (N:P:K, 20:20:20) plus iron chelate and micronutrients. Apical buds of vegetative stems (3–7 weeks old) were used for the preparation of glandular trichome cells for enzyme extraction and for nucleic acid isolation. (−)-4S-Limonene (97%) and other monoterpene standards were part of the lab collection or were purchased from Sigma or Aldrich and were purified by standard chromatographic methods.

Limonene-6-hydroxylase isolation—Limonene-6-hydroxylase was extracted from a purified preparation of glandular trichome secretory cell clusters isolated from spearmint (*Mentha spicata*). To obtain these clusters, plant material was soaked in ice-cold, distilled water for 1 h and gently abraded in a cell disrupter of our own design (Colby et al., *J. Biol. Chem.* 268:23016–23024 [1993]). Batches of 45–60 g of spearmint apical tissue were abraded in the 600 ml polycarbonate cell disruption chamber with 140 ml of glass beads (500 $\mu$m diameter, Bio-Spec Products), 35 g Amberlite XAD-4 resin and ~300 ml of extraction buffer consisting of (25 mM MOPSO, 0.5 mM sodium phosphate (pH 7.4), 200 mM sorbitol, 10 mM sucrose, 10 mM sodium-metabisulfite, 10 mM ascorbate, 1% (w/v) polyvinylpyrrolidone ($M_r$ 40,000), 0.6% methyl cellulose, and 1 mM DTT). Removal of glandular trichome secretory cells was accomplished by three 1 min pulses of operation with the rotor speed controlled by a rheostat set at 85–95 V. This procedure was carried out at 4° C., and after each pulse the chamber was allowed to cool for 1 min. The isolated secretory cell clusters were separated from the glass beads, XAD-4 resin and residual plant material by sieving through a series of nylon meshes. The secretory cell clusters (approximately 60 $\mu$m in diameter) readily passed through meshes of 350 and 105 $\mu$m and were collected on a mesh of 20 $\mu$m. After filtration, cell clusters were washed to remove chloroplasts and other contaminates, and suspended in 50 ml of cell disruption (sonication) buffer (100 mM sodium phosphate (pH 7.4), 250 mM sucrose, 1 mM DTT, 1 mM PMSF, 1 mM sodium EDTA, and 5 $\mu$m flavins (FAD and FMN)). Suspensions (50 ml) of isolated secretory cell clusters (~1.6×10$^6$ cells/ml) were disrupted by sonication in the presence of 25% (v/v) XAD-4 resin and 0.5–0.9 g of Polyvinylpolypyrrolidone (added based on the level of phenolics observed during tissue harvesting) with the probe (Braun-Sonic 2000) at maximum power; five times for 15 sec with 1 min cooling periods between each 15 sec burst. After sonication, protein was extracted by gentle stirring at 4° C. for 20 min. The resulting extract was filtered through, and washed on, a 20 $\mu$m nylon mesh on a Buchner funnel under vacuum to remove XAD-4 beads, PVPP, and cell debris. The resulting filtrate (~80 ml) was homogenized in a chilled Tenbroek glass homogenizer and brought to 100 ml with sonication buffer. The sonicate was then centrifuged at 18,000×g to remove cellular debris and the resulting supernatant was centrifuged at 195,000×g to yield the glandular microsomal fraction. Microsomal pellets prepared from gland sonicates (originating from 110 g of spearmint apical tissue) were resuspended and homogenized in 6 ml of solubilization buffer (25 mM Tris (pH 7.4), 30% glycerol, 1 mM DTT, 1 mM EDTA, 20 mM octylglucoside) and incubated on ice at 4° C. overnight (under $N_2$). Insoluble material was removed by centrifugation at (195,000×g) for 90 min at 4° C. to provide the soluble supernatant used as the enzyme source for further purification.

Example 2

(–)-Limonene-6-hydroxylase purification

The solubilized protein fraction from Example 1 containing the (–)-limonene-6-hydroxylase was subjected to two rounds of hydrophobic interaction chromatography on methyl-agarose (Sigma Lot #97F9710, Aug. 6, 1992), followed by further purification by SDS-PAGE (Laemmli, *Nature* 227:680–685 [1970]). Hydrophobic interaction chromatography was performed at room temperature. Samples were kept on ice before loading and as fractions were collected. Typically, 3 to 6 nmol of solubilized cytochrome P450 measured by the method of Omura and Sato (Omura et al., *J. Biol. Chem.* 239:2379–2385 [1964]) were loaded onto a 3 ml methyl-agarose column (C-1), that was prepared and equilibrated with solubilization buffer. The flow-through of the first C-1 column (12 ml) was collected and loaded onto a second C-1 column (equilibrated as before). Following the removal of contaminants achieved on the first C-1 column, the cytochrome P450 bound to the second column and was selectively eluted with solubilization buffer plus substrate (2 $\mu$l/ml (–)-limonene mixed to an emulsion in buffer). Although this procedure proved useful for purification of the (–)-limonene-6-hydroxylase and for obtaining amino acid micro-sequence data from the pure enzyme, it was not reproducible with additional lots of methyl-agarose from Sigma and recovery yields varied greatly between individual protein preparations. To establish this example, it was therefore necessary to develop an alternative, reproducible protein purification strategy which is described for the first time in the following paragraph.

Alternative protein purification method—Microsomal pellets prepared from gland sonicates originating from 200–250 g of spearmint leaves (16–20) were resuspended in 5 ml of 25 mM HEPES buffer (pH 7.2), containing 20% glycerol, 25 mM KCl, 10 mM $MgCl_2$, 5 mM DTT, 0.2 mM PMSF, 50 $\mu$M BHT, and 10 mg/liter leupeptin using a glass Tenbroeck homogenizer. An equal volume of the same buffer containing 1% Emulgen 911 was added slowly dropwise while stirring on ice, and the stirring continued for 1 h. The suspension was then centrifuged for 90 min at 195,000× g. The resulting solubilized microsomes were used as the source of (–)-limonene hydroxylase for further purification, which consisted of a polyethylene glycol, (PEG) precipitation step followed by anion-exchange chromatography on DEAE Sepharose and chromatography on ceramic hydroxyl-apatite (the latter serves a dual function as a final purification step and a detergent removal step which is required to reconstitute (–)-limonene-6-hydroxylase catalytic activity in homogeneous protein preparations).

A 60% suspension of polyethylene glycol ($M_r$ 3,350) in HEPES buffer (above) with out detergent was added slowly dropwise to the solubilized microsomes while stirring on ice to give a final PEG concentration of 30%; stirring was continued for 30 min. The suspension was then centrifuged at 140,000×g for 60 min and the supernatant discarded. The resultant 0–30% PEG pellet was then resuspended in 5 ml of buffer containing 25 mM Tris-Cl (pH 7.0), 20% glycerol, 1 mM DTT and 50 $\mu$M BHT using a glass homogenizer. To this suspension was slowly added (dropwise) an equal volume of the same buffer containing 0.2% Emulgen 911 followed by stirring on ice for an additional 30 min. The suspension was then clarified by centrifugation at 140,000×g for 30 min.

The clarified PEG suspension was applied to a 3.5×1.75 cm column of DEAE Sepharose (Sigma or Pharmacia) equilibrated and washed with buffer (25 mM Tris-Cl (pH 7.0) containing 20% glycerol, 1 mM DTT, 50 $\mu$M BHT, and 0.1% Emulgen 911), at a rate of 1.75 ml/min. The remaining bound protein was eluted stepwise (75 ml/step) with the same buffer containing 50, 125, 250, and 1000 mM KCl. DEAE anion-exchange chromatography performed in this manner yields 45–60% of the microsomal P-450 measured by the method of Omura and Sato (Omura, supra) as an essentially homogeneous 57 kD protein (with a 21% P-450 yield relative to the glandular sonicate). Cytochrome P-450 containing fractions from the anion-exchange column were concentrated by Amicon YM-30 ultrafiltration (Amicon) and bound to ceramic hydroxylapatite (Sigma). Emulgen 911 was removed by washing the matrix with 5 mM potassium, 40 $\mu$m (Bio-Rad Laboratories) phosphate buffer (pH 7.4) containing 20% glycerol, 1 mM DTT, and 10 mM CHAPS. The matrix was further washed with the same phosphate buffer containing no detergent, after which the (–)-limonene-6-hydroxylase is eluted from hydroxylapatite with 240 mM potassium phosphate buffer containing 20% glycerol and 1 mM DTT.

Purified cytochrome P-450-containing fractions were combined and concentrated by TCA precipitation in preparation for SDS-PAGE. This protocol was shown to provide pure samples suitable for amino acid sequence analysis. TCA was added to protein samples at 8% (v/v), and the mixture was vigorously vortexed and incubated on ice for 40 min. Precipitated protein was pelleted by centrifugation for 15 min at 10,000×g at 4° C. The pellets were washed twice with ice cold acetone and vacuum desiccated to remove traces of organic solvent. The resulting pellets were resuspended in 75 µl of 1× Laemmli loading buffer (Laemmli, supra), frozen at −80° C. overnight and then heated for 15 min at 55° C. prior to SDS-PAGE.

Example 3

Amino acid analysis and protein sequencing

For obtaining N-terminal amino acid sequence data, the gels were electroblotted to polyvinyldifluoride membranes (Immobilon-P$^{SQ}$, Millipore) in 25 mM Tris, 192 mM glycine (pH 8.3) containing 20% (v/v) methanol (Towbin et al., *Proc. Natl. Acad. Sci. USA* 76:4350–4354 [1979]). Membranes were stained in 0.1% Coomassie Brilliant Blue R-250 in (methanol:acetic acid:water (50:10:40, v/v/v)) and destained with methanol:acetic acid:water (50:5:45). The resolved bands containing cytochrome P450 at ~57 kDa ((−)-limonene-6-hydroxylase) were excised, washed by vortexing in distilled water, and the membrane fragments containing the target proteins were subjected to sequence analysis via edman degradation on an Applied Biosystems 470 sequenator (at The Washington State University Laboratory for Bioanalysis and Biotechnology, Pullman, Wash.).

In order to obtain internal amino acid sequence information, protein samples were subjected to SDS-PAGE as described above. In this case, however, the gels were not directly electroblotted but were visualized by staining with 0.2% Coomassie Brilliant Blue R-250 in methanol:acetic acid:water (30:10:60, v/v/v) and destained with methanol:acetic acid:water (5:8:93, v/v/v) to avoid gel shrinkage. The gel band at 57 kDa was excised, washed with distilled water, and equilibrated in SDS-sample buffer (Laemmli, supra) for 5 min at room temperature. In a second SDS-PAGE step, the gels were polymerized with an extra large stacking gel and pre-electrophoresed as described above. The equilibrated gel slices from above were inserted into the sample well of the second SDS-10% polyacrylamide vertical slab gel (16 cm×18 cm×1.0 mm) which was previously filled with SDS-running buffer (Laemmli, supra). V-8 protease (2 µg) from Sigma was added to SDS sample buffer with 20% (v/v) glycerol and loaded using a Hamilton syringe into the sample well surrounding the gel slice. The samples were electrophoresed at 90 V (~⅔ of the way into the stacking gel). The power was turned off for 30 min in order to allow proteolytic cleavage. Electrophoresis was then continued at 90 V until the Bromophenol Blue dye front had entered the resolving gel. At this time, cooling was maintained at 20° C. and electrophoresis was continued at 20 mA constant current for ~3 h. Following electrophoresis, the gel was electroblotted, the resulting membrane was coomassie stained, and the resolved peptide bands were prepared for microsequence analysis as described above. This method of proteolytic cleavage routinely yielded three peptide fragments whose combined molecular weights equaled approximately 57 kDa.

Peptides were sequenced via Edman degradation on an Applied Biosystems 470 sequenator at the Washington State University Laboratory for Bioanalysis and Biotechnology, Pullman, Wash.

These methods yielded 20–25 residues of amino acid sequence data from each of the three V-8 derived peptides, as well as from the N-terminus of uncleaved (native) protein. The sequence data from the second largest proteolytic peptide (V-8.2, SEQ ID No:3) was identical to that of the uncleaved protein representing the N-terminus of the native enzyme. The V-8.3 (SEQ ID No:4) sequenced fragment could be most easily aligned with the C-terminal region of an avocado P450 (Bozak et al., *Proc. Natl. Acad. Sci. USA* 87:3904–3908 [1990]) suggesting its origin from the same C-terminal region on the (−)-limonene hydroxylase. The third peptide fragment (V-8.1, SEQ ID No:2) was assumed to be located somewhere between V-8.2 and V-8.3. [The avocado P450 was not a useful probe for limonene hydroxylases as it was not sufficiently similar].

Example 4

PCR-based Probe Generation

Degeneracy considerations prevented the direct use for library screening of the amino acid sequence data generated from the purified (−)-limonene-6-hydroxylase from spearmint. PCR methods were employed to amplify the nucleotide sequences corresponding to the amino acid data. Six short, degenerate PCR primers were designed to prime the termini of each encoded peptide fragment. These primers are shown in the following Table 1:

TABLE 1

PCR Primers

| Primer Name | Primer Sequence (5' to 3') | SEQ ID No. |
|---|---|---|
| 1.AC | GTI ACI AAA ATG AC<br>     TG    G      T | 10 |
| 1.AG | GTI ACI AAA ATG AG<br>     TG    G      T | 11 |
| 1.B | GC CTC IGA ICC CTG ATC CTT<br> T     CT    T    G   T | 12 |
| 1.C | G TGT GTC GTC GTG TGC AGG GCG GCG TTC G | 13 |
| 2.AA | ATG GAG CTI GAC CTI CTI A<br>      A T G    T T G T G<br>         A       A   A | 14 |

TABLE 1-continued

PCR Primers

```
Primer
Name    Primer Sequence (5' to 3')                              SEQ ID No.

2.AT    ATG GAG CTI GAC CTI CTI T                                   15
                A T G     T T G T G
                A           A A

2.B     TC IAT ATA IGT IGC IAC                                      16
                          G

3.A     ATG GAG GTI AAC GGI TAC AC                                  17
                A         T       T

3.B     TTT TTT TTT TTT TTT TTT A                                   18
                                T
                                C

3.C     CC GAT IGC GAT IAC GTT IAT AAA AAT ICT IGT CTT IGC IGG      19
              T   T       A         G   G   G   T
              A   A                     T
```

I = Inosine

Primer 1.AC was designed to prime the 5' end of the proteolytic peptide fragment V-8.1 in the forward orientation. This primer was combined with primer 1.AG during PCR to create the 1.A primer which was successfully employed to amplify the 75 bp nucleotide sequence encoding the V-8.1 peptide fragment.

Primer 1.AG was designed for the same purpose as primer 1.AC. Primers 1.AC and 1.AG were synthesized separately and combined to create the primer 1.A in order to reduce the population degeneracy level in the primer pool.

Primer 1.C primes the central region of the V-8.1 peptide fragment. This primer is a non-degenerate primer oriented in the forward direction and was successfully employed when combined with the primer 3.C to amplify the nucleotide sequence spanning the V-8.1 and V-8.3 proteolytic peptide fragments. The amplified nucleotide sequence was utilized as a cDNA hybridization probe and named LH-1.

Primer 2.AA was designed to prime the amino-terminus of the nucleotide sequence based on the 5' end of the V-8.2 peptide fragment. This primer is oriented in the forward direction and was combined with the primer 2.AT during PCR to achieve a lower degeneracy level in the primer pool.

Primer 2.AT was designed for the same purpose and at the same location as the primer 2.AA.

Primer 2.B was designed to prime the 3' end of the V-8.2 peptide fragment in the reverse orientation.

Primer 3.A designed to prime the 5' end of the V-8.3 peptide fragment in the forward direction.

Primer 3.B primes the poly(A) tail on cDNA molecules. This primer was designed in the reverse orientation to amplify nucleotide fragments when combined with any of the other forward primers.

Primer 3.C was designed to prime the 3' end of the V-8.3 peptide fragment in the reverse orientation.

Additional primers were designed to amplify regions spanning the three peptide fragments.

The PCR primers were employed in all possible combinations with a range of amplification conditions using spearmint gland cDNA as template. Analysis of PCR products by gel electrophoresis indicated that one primer set (1.A and 1.B) had amplified the appropriate sized DNA fragment corresponding to the V-8.1 peptide. This 75 bp fragment was cloned into pT7Blue (Novagen), sequenced (by the chain termination method using Sequenase Version 2.0, United States Biochemical Corp.), and shown to code for the V-8.1 peptide. A non-degenerate forward primer (1.C) was then designed from the internal coding sequence of V-8.1 (SEQ ID No:2) which, when combined with the degenerate reverse primer 3.C (SEQ ID No: 19) designed to the V-8.3 peptide (SEQ ID No:4), permitted the amplification of a specific 700 bp DNA fragment. This fragment was cloned in to pT7Blue and sequenced as above, confirming that it coded for the sequence which spanned the V-8.1 and V-8.3 peptides. This fragment (LH-1, SEQ ID No:6) was then labeled with [$\alpha$-$^{32}$P-dATP] via the random hexamer reaction (Tabor et al., in *Current Protocols in Molecular Biology*. Sections 3.5.9-3.5.10, John Wiley and Sons inc. New York [1991]) and was used as a hybridization probe to screen the spearmint oil gland cDNA library.

Example 5

Plasmid Formation and Screening cDNA Library Construction—Spearmint (*Mentha spicata*) and peppermint (*Mentha piperita*) oil gland specific cDNA libraries were constructed. As published (Gershenzon et al., *Anal. Biochem.* 200:130–138 [1992]), the glandular trichome secretory cell isolation procedure does not protect RNA from degrading during a long water imbibition prior to surface abrasion. To protect RNA from degradation, published RNA purification protocols require either immediate freezing of tissue in liquid nitrogen or immersion in either strong organic solvents or chaotropic salts. (see prior RNA isolation methods submitted with limonene synthase patent) These protocols have proven themselves to be incompatible with gland cluster isolation. Additionally, most tissues do not have the high levels of RNA degrading phenolics found in mint secretory glands. Therefore, a reproducible procedure was developed that protects the RNA from degradation during leaf imbibition and subsequent gland isolation and extraction. Additions of the low molecular weight RNase inhibitor, aurintricarboxylic acid (ATCA) (Gonzales et al., *Biochemistry* 19:4299–4303 [1980]) and the low molecular weight polyphenyloxidase inhibitor, thiourea (Van Driessche et al., *Anal. Biochem.* 141:184–188 [1984]), to the water used during imbibition were tested. These additions were shown not to adversely effect water imbibition and gland isolation, yet to greatly improve the yield and quality of subsequent RNA isolation. Optimum concentrations for ATCA and thiourea were found to be 5 mM and 1 mM, respectively. These modifications allowed gland clusters to be isolated that consistently contained undegraded RNA. RNA extraction and purification using the improved method of Logemann et al. (Logemann et al., *Anal. Biochem.* 163:16–20 [1987]) was compromised by phenolics released during initial disruption of the purified gland cells. The inclusion of insoluble polyvinyl-polypyrrolidone (PVPP) (Lewinsohn et al., *Plant Mol. Biol. Rep.* 12(1):20–25 [1994]) to the RNA extraction buffer of Logemann et al., sufficiently sequestered phenolics and eliminated degradation. These modifications to the gland cell cluster isolation and RNA purification protocols consistently yield intact RNA that is useful for further manipulation. Poly (A)+ RNA was isolated on oligo (dT)-cellulose (Pharmacia Biotech, Inc.), and 5 µg of the resulting purified mRNA was utilized to construct a λZAP cDNA library for each Mentha species according to the manufacturer's instructions (Stratagene).

Spearmint gland cDNA Library Screening—The 700 bp nucleotide probe (LH-1, SEQ ID No:6) generated by the PCR strategy of Example 4 was employed to screen replicate filter lifts of 1×10$^5$ primary plaques grown in *E. coli* XL1-Blue MRF' using Strategene protocols. Hybridization according to the DuPont-New England Nuclear protocol was for 24 h at 65° C. in 25 ml of hybridization solution consisting of 5× SSPE (1× SSPE=150 mM NaCl, 10 mM sodium phosphate, and 1 mM EDTA), 5× Denhardts, 1% SDS and 100 µg/ml denatured sheared salmon sperm DNA. Blots were washed twice for 10 min with 2× SSPE at room temperature, twice with 2× SSPE containing 2% SDS for 45 min at 65° C., and, finally, twice with 0.1× SSPE for 15 min at room temperature.

Of the plaques affording positive signals, 35 were purified through two additional cycles of hybridization. Thirty pure clones were in vivo excised as Bluescript SK (−) phagemids and their insert sizes were determined by PCR using T3 and T7 promoter primers. The largest 6 clones (~1.6 kb) were partially sequenced using T3 and T7 promoter primers. Three of these cDNA clones, 8A, 11A and 22C, were completely sequenced using nested deletion subclones generated with the Exo III/MungBean Nuclease Deletion Kit (Stratagene) as per manufacturer's instructions; additional sequencing primers, shown in the following Table 2 were also employed.

TABLE 2

Sequencing Primers

| Designation | Sequence | | SEQ ID No. |
|---|---|---|---|
| 22CR3 | CACGACATCTTCGACACCTCCTCC | | 20 |
| 22CF1 | GCAACCTACATCGTATCCCTCC | ** | 21 |
| NTREV1 | GGCTCGGAGGTAGGTTTTGTTGGG | | 22 |
| NTREV2 | GATTAGGAGGGATACGATGTAGGTTGC | | 23 |
| 11A4.25R6 | CTGGGCTCAGCAGCTCTGTCAA | | 24 |
| 4.25R5 | GGGCTCAGCAGCTCTCTC | | 25 |
| 4.25R3 | CTTCACCAACTCCGCCAACG | ** | 26 |

TABLE 2-continued

Sequencing Primers

| Designation | Sequence | SEQ ID No. |
|---|---|---|
| 11A4.25R2 | GCTCTTCTTCTCCCTATGC | 27 |
| 11A4.25R | TAGCTCTTGCACCTCGCTC | 28 |
| 11A.1F4 | TTCGGGAGTGTGCTCAAGGACCAGG | 29 |
| 11A1F3 | GTTGGTGAAGGAGTTCGCTG | 30 |
| 11A.1F2 | CTTACAACGATCACTGG | 31 |
| S12.2PF1 | GACATCGTCGACGTTCTTTTCAGG | 32 |
| S12.2PF2 | CTACCACTTCGACTGGAAATTGC | 33 |
| S12.2PF3 | CTGAGATCGGTGTTAAAGGAGAC | 34 |
| S12.2PR1 | GCCACCTCTATAAGACACTCCTC | 35 |
| S12-2PR2 | GATCTCAACATTTGCCAGC | 36 |
| S12BF | GAAACCATGGAGCTCGACC | 37 |
| P17.1F2 | CGACGACATCATCTTCAGC | 38 |
| P17F1 | AGTACGGTCCAGTGGTGCACGTGC | 39 |
| P17.1.2F3 | GAGGAGCTGGTGGAGCTGGTGAAG | 40 |
| P17.1.2F5 | CGAGATCATGCAGAGAAGAATGC | 41 |
| P17R1 | ATGGGACCTCAACATTTGGCAAC | 42 |
| P17.1R2 | ATGTTCTTGGCCTTATTCG | 43 |
| P17.1.2R4 | CAGAGCAAGTTGAGGAGCTTGGAGG | 44 |
| P17.1.2F4 | CCATCACCACCAACGCCATCAAAGC | 45 |
| P17.1.2R6 | GTACTGCTTCGCCACGCTGG | 46 |
| BLUT3 | CGCGCAATTAACCCTCACTAAAGGG | 47 |
| 11A4.10F | GCTGAATGGGCAATGG | 48 |
| 11A.1F-A | CACCTCCACTTCCTGTGG | 49 |
| P17.1.2R5 | GCTGAAGAGCTCGGAGACGCAGATC | 50 |

**These primers were used as PCR primers to construct the cDNA hybridization probe LH-2 in addition to being used as sequencing primers.

DNA fragments were assembled, and the sequence was analyzed using Seq AID II version 3.8 (a public domain program provided by Rhodes, D. D., and Roufa, D. J., Kansas State University) and the Genetics Computer Group Packet (The Genetics Computer Group, *Program Manual for the Wisconsin Packet, Version* 8, Genetics Computer Group, Madison, Wis. [1994]). Following alignment of the cDNA sequences with the peptide sequences obtained, it was determined that all three of these cDNA clones were truncated at the N-terminus; clone 22C was also truncated at the C-terminus and clone 8A was shuffled. Therefore, a second nucleotide probe (LH-2, SEQ ID No:7) was generated by PCR using a new forward primer (22CF, SEQ ID No:21), homologous to the 20 most N-terminal bases of clone 22C and a new reverse primer 4.25R3, SEQ ID No:26 (priming a region 500 bp downstream on clone 22C). The resulting DNA fragment (probe LH-2, SEQ ID No:7) was employed to re-screen the spearmint gland library as above. The second screen yielded 30 purified clones, which were in vivo excised and partially sequenced (Dye Deoxy Terminator Cycle Sequencing, Applied Biosystems). A single full-length clone, designated pSM12.2, was isolated (1762 bp in length) and found to encode the entire protein by comparison to the original amino acid sequence data.

Isolation of peppermint cytochrome P450 cDNA clones—One hundred thousand primary (peppermint gland cDNA) plaques were grown and screened by hybridization with probe LH-2 (SEQ ID No:7) employing the same methods, as described above, used to isolate the spearmint cDNA clone pSM12.2. Of the 25 plaques that were purified, ten were in vivo excised and partially sequenced with T3 and T7 promoter primers. Sequence alignment indicated that seven of these were representatives of the same gene (one of which, pPM17, was a full length clone and was completely sequenced). The nucleotide sequences for both cloned inserts (pSM12.2, (−)-limonene-6-hydroxylase, SEQ ID No:5, and pPM17, (−)-limonene-3-hydroxylase, SEQ ID No:8) are shown in FIGS. 4 and 5, respectively. The amino acid sequence alignment encoded by clones pSM12.2, SEQ ID No: 1 obtained as described in Example 3, and pPM17, SEQ ID No:9 as deduced from the nucleotide sequence of SEQ ID No:8, are shown in FIG. 7.

Baculovirus Constructs—Site directed mutagenesis PCR was employed to subclone the (−)-limonene-6-hydroxylase cDNA (pSM12.2, SEQ ID No:5) into the baculovirus transfer vector pBlueBac3 (Invitrogen). PCR primers (see Table 3, below) were designed to add restriction sites (NcoI) at the 5' translation initiation codon extending to a second primer at a position 20 bp downstream of the translation termination codon, thus creating a HindIII site. The resulting fragment was digested, gel purified, ligated into NcoI-HindIII restricted pBlueBac3, and transformed into E. coli DH5α cells, thus creating the baculovirus transfer vector pBac12.2.

TABLE 3

PCR Primers used to construct the baculovirus transfer vectors pSM12.2 and pPM17.35:

| Designation | Sequence | SEQ ID No. |
|---|---|---|
| pE17Start | ATGGAGCTTCAGATTTCG | 51 |
| pE17Stop | GCACTCTTTATTCAAAGG AGC | 52 |
| S12BF | GAAACCATGGAGCTCGACC | 53 |
| S12BR | TATGCTAAGCTTCTTAGTGG | 54 |
| BAC4PCR-F | TTTACTGTTTTCGTAACAGTTTTG | 55 |
| BAC4PCR-R | CAACAACGCACAGAATCTAGC | 56 |
| BAC3PCR-F | TTTACTGTTTTCGTAACAGTTTTG | 57 |
| BAC3PCR-R | CAACAACGCACAGAATCTAGC | 58 |

The (−)-limonene-3-hydroxylase cDNA (pPM17, SEQ ID No:8) was cloned into the baculovirus transfer vector pBlueBac4 (Invitrogen) by PCR using the thermal stable, high fidelity, blunting polymerase Pfu I (Stratagene) with PCR primers pE17Start (at the translation initiation ATG) and pE17Stop (extending 21 bp downstream of the translation termination codon) into the 3' untranslated region. The resulting blunt-ended fragment was ligated into Nhe I digested pBlueBac4 (Invitrogen), that had been filled in via Klenow enzyme (Boehringer Mannheim), and was transformed into E. coli DH5α, thus yielding the baculovirus transfer vector pBac17.35. Both transfer vectors were completely resequenced to verify cloning junctions; no errors were introduced by polymerase reactions.

Recombinant baculovirus was constructed as described by Summers and Smith (Summers et al, *A Manual of Methods for Baculovirus Vectors and Insect Cell Culture Procedures*, Bulletin No. 1555, Texas Agricultural Experiment Station, College Station, Tex. [1988]). Briefly, CsCl banded transfer vector was cotransfected into *Spodoptera frugiperda* (Sf9) cells with purified, linearized AcMNPV DNA by the method of cationic liposome mediated transfection (Invitrogen) as per the manufacturer's instructions. Recombinant virus was identified by the formation of blue (occlusion negative) plaques using established plaque assay procedures (Summers et al., supra; O'Reilly et al., *Baculovirus Expression Vectors, A Laboratory Manual*, Oxford: Oxford University Press, pp. 45–50, 109–166 [1994]; Smith et al., *Lancet* 339:1375–1377 [1992]). Putative recombinant viruses were monitored for purity by PCR analysis and gel electrophoresis.

Example 6 cDNA Expression

Sf9 Cell Culture and Recombinant Protein Expression—*Spodoptera frugiperda* (Sf9) cells were maintained as monolayers or in suspension (85–90 RPM) culture at 27° C. in Grace's media (Gibco BRL supplemented with 600 mg/L L-glutamine, 4 g/L yeastolate, 3.3 g/L lactoalbumin hydrolyste, 10% (v/v) fetal bovine serum, 0.1% pluronic F-68, and 10 µg gentamicin/ml). For the generation of high titer viral stocks, suspension cultures of log phase cells (1.1 to $1.6 \times 10^6$ cells/ml) were infected at a multiplicity of infection (MOI) equal to ~0.1 PFU/cell, and then allowed to grow until near complete cell lysis had occurred. Cell debris was pelleted by centrifugation and the media stored at 4° C. For expression, log phase suspension cultures of Sf9 cells were supplemented with 3 µg hemin chloride/ml (Sigma) in 75 mM sodium phosphate and 0.1 N NaOH (pH 7.6) and infected with recombinant baculovirus at an MOI of between 5 and 10 PFU/cell. The addition of hemin to the culture media was required to compensate for the low heme synthetic capability of the insect cells. Cells were harvested at various time intervals (between 24 and 96 hours post infection) by centrifugation (800×g, 10 min), then washed with PBS, and resuspended in 75 mM sodium phosphate buffer (pH 7.4) containing 30% glycerol, 1 mM DTT, and 1 mM EDTA.

Example 7

Limonene Hydroxylase Analysis

Product analysis and other analytical methods—An in situ bioassay was developed to evaluate functional expression of (−)-limonene hydroxylase activity. Expression cultures were incubated in the presence of ~300 µM (−)-(4S)-limonene, which was added to the culture medium immediately following infection. At zero and various time intervals, 50–100 ml culture samples were removed and cells were harvested by centrifugation, washed, and resuspended in 3–6 ml of sodium phosphate buffer as described above. Resuspended cell suspensions were chilled on ice and extracted twice with 3 ml portions of ice cold ether after the addition of 25 nmol camphor as internal standard. The extract was decolorized with activated charcoal, backwashed with water, and the organic phase containing the products was passed through a short column of anhydrous $MgSO_4$ and activated silica. The purified extracts were then concentrated to ~500 µl under $N_2$ and analyzed by capillary GLC (Hewlett-Packard 5890). GLC was performed on 0.25 mm i.d.×30 m of fused silica capillary columns coated with superox FA or AT-1000 using "on column" injection and flame ionization detection with $H_2$ as carrier gas at 13.5 psi (programmed from 45° C. (5 min) to 220° C. at 10° C. per min). The identities of the products, (−)-trans-carveol from C-6 hydroxylation and (−)-trans-isopiperitenol from C-3 hydroxlyation, were confirmed by coincidence of retention times with the corresponding authentic standard. Peak quantitation was by electronic integration based on the internal standard.

Functional expression of the (−)-limonene-6-hydroxylase (pSM12.2) from spearmint and the (−)-limonene-3-hydroxylase from peppermint (pPM17) using the in situ bioassay thus confirmed the identity of the clones. GLC and GLC-MS analysis of Sf9 expression cultures infected with Baculovirus clones pBac12.2 and pBac17.35 verified the production of between 15 and 35 nmol of the expected oxygenated monoterpene product ((−)-trans-carveol from the spearmint clone and (−)-trans-isopiperitenol from the peppermint clone) per 50 ml of expression culture. Non-infected Sf9 control cultures grown under expression conditions and fed limonene substrate, control cultures infected with recombinant baculovirus but not fed limonene, and Sf9 cells alone evidenced no detectable carveol or isopiperitenol production, as expected. Cell free extracts of the transfected cells yielded a typical CO-difference spectrum (Omura et al., *J. Biol. Chem.* 239:2379–2385 [1964]) and afforded a positive Western blot (using antibody directed against the native spearmint 6-hydroxylase) thus demonstrating the recombinant enzymes to resemble their native counterparts, which have been previously isolated and characterized (but not previously purified) from the respective mint species (Karp et al., *Arch. Biochem. Biophys.* 276:219–226 [1990]), and confirming that the isolated genes are those controlling the oxidation pattern of limonene in monoterpene metabolism (Gershenzon et al., *Rec. Adv. Phytochem.* 28:193–229 [1994]).

While the preferred embodiments of the invention have been illustrated and described, it will be appreciated that various changes can be made therein without departing from the spirit and scope of the invention. For example, sequence variations from those described and claimed herein as deletions, substitutions, mutations, insertions and the like are intended to be within the scope of the claims except insofar as limited by the prior art.

The embodiments of the invention in which an exclusive property or privilege is claimed are defined as follows:

1. An isolated nucleic acid molecule encoding limonene-6-hydroxylase from *Mentha spicata*.

2. An isolated nucleic acid molecule encoding limonene-3-hydroxylase from *Mentha piperita*.

3. An isolated nucleic acid molecule encoding a protein having the biological activity of SEQ ID No:1 or SEQ ID No:9.

4. An isolated nucleic acid molecule of claim 3 which encodes the amino acid sequence of SEQ ID No: 1 or SEQ ID No:9.

5. An isolated nucleic acid molecule of claim 3 which encodes the amino acid sequence of SEQ ID No:1.

6. An isolated nucleic acid molecule of claim 3 which encodes the amino acid sequence of SEQ ID No:9.

7. An isolated nucleic acid molecule of claim 3 having the sequence of SEQ ID No:5.

8. An isolated nucleic acid molecule of claim 3 having the sequence of SEQ ID No:8.

9. A replicable expression vector comprising a nucleotide sequence encoding a protein having the biological activity of SEQ ID No:1 or SEQ ID No:9.

10. An replicable expression vector of claim 9 wherein the nucleotide sequence comprises the sequence of SEQ ID No:5 or SEQ ID No:8.

11. A host cell comprising a vector of claim 9.

12. A host cell comprising a vector of claim 10.

13. A method of enhancing the production of limonene-6-hydroxylase in a suitable host cell comprising introducing into the host cell an expression vector of claim 9 that comprises a nucleotide acid molecule encoding a protein having the biological activity of SEQ ID No:1 under conditions enabling expression of the protein in the host cell.

14. A method of enhancing the production of limonene-3-hydroxylase in a suitable host cell comprising introducing into the host cell an expression vector of claim 9 that comprises a nucleotide acid molecule encoding a protein having the biological activity of SEQ ID No:9 under conditions enabling expression of the protein in the host cell.

* * * * *

UNITED STATES PATENT AND TRADEMARK OFFICE
CERTIFICATE OF CORRECTION

PATENT NO. : 6,083,731
DATED : July 4, 2000
INVENTOR(S) : R.B. Croteau et al.

It is certified that error appears in the above-identified patent and that said Letters Patent is hereby corrected as shown below:

Column 1, page 1, [56],
References Cited, (Other References, Item 2) "4S(Limonene" should read -- 4S-Limonene --
References Cited, (Other References, Item 4) "λ-Terpinene" should read -- γ-Terpinene --
References Cited, (Other References, Item 13) "Monterpenes," should read -- Monoterpenes, --

Column 2, page 1, [56],
References Cited, (Other References, Item 14) before "Rodriguez" insert -- E. --
References Cited, (Other References, Item 16) ""the" should read -- "The --
References Cited, (Other References, Item 16) "*In*" should read -- In --
References Cited, (Other References, Item 16) delete "of the International" second occurrence
References Cited, (Other References, Item 18) "57(S1);10-14" should read -- 57(S1):10-14 --

Column 1, page 2, [56],
References Cited, (Other References, Item 25) "Cis-(+)-and (+)-trans-" should read -- (+)-*cis*-and(+)-*trans*- --
References Cited, (Other References, Item 29) "Mentha" should read -- *Mentha* --

Column 2, page 2, [56],
References Cited, (Other References, Item 31) "Mentha" should read -- *Mentha* --
References Cited, (Other References, Item 32) "crtE" should read -- *crtE* --
References Cited, (Other References, Item 39) "Chromatography" should break as follows -- Chromato-graphy --
References Cited, (Other References, Item 42) "Mentha" should read -- *Mentha* --

Column 3,
Line 29, "pSM 12" should read -- pSM12 --
Line 34, "V-8.1(SEQ" should read -- V-8.1 (SEQ --

Column 7,
Lines 19-20, "unrmutated" should read -- unmutated --

Column 13,
Line 29, "BgII" should read -- BglI --

UNITED STATES PATENT AND TRADEMARK OFFICE
CERTIFICATE OF CORRECTION

PATENT NO. : 6,083,731
DATED : July 4, 2000
INVENTOR(S) : R.B. Croteau et al.

It is certified that error appears in the above-identified patent and that said Letters Patent is hereby corrected as shown below:

Column 14,
Line 15 "No.27,325)" should read -- No. 27,325) --
Line 28, "(His)$_6$.Tag" should read -- (His)$_6$.Tag --

Column 17,
Line 16, "5 $\mu$m" should read -- 5 $\mu$M --

Column 19,
Line 33-34, "methano-l:acetic" should break as follows -- methanol: acetic --

Signed and Sealed this

Twenty-fifth Day of September, 2001

Attest:

NICHOLAS P. GODICI
Attesting Officer
Acting Director of the United States Patent and Trademark Office